(12) United States Patent
Gartel et al.

(10) Patent No.: US 8,207,136 B2
(45) Date of Patent: Jun. 26, 2012

(54) NUCLEOSIDE COMPOUNDS AND METHODS OF USE THEREOF

(75) Inventors: Andrei Gartel, Chicago, IL (US); Senthil K. Radhakrishnan, Pasadena, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1055 days.

(21) Appl. No.: 11/912,820

(22) PCT Filed: Apr. 26, 2006

(86) PCT No.: PCT/US2006/015834
§ 371 (c)(1),
(2), (4) Date: May 9, 2008

(87) PCT Pub. No.: WO2006/116512
PCT Pub. Date: Nov. 2, 2006

(65) Prior Publication Data
US 2009/0117651 A1 May 7, 2009

Related U.S. Application Data

(60) Provisional application No. 60/674,744, filed on Apr. 26, 2005, provisional application No. 60/703,541, filed on Jul. 29, 2005, provisional application No. 60/738,736, filed on Nov. 22, 2005.

(51) Int. Cl.
*A01N 43/04* (2006.01)
*A61K 31/70* (2006.01)
(52) U.S. Cl. ............................. 514/43; 514/42
(58) Field of Classification Search .................. None
See application file for complete search history.

(56) References Cited

U.S. PATENT DOCUMENTS

2004/0110717 A1  6/2004  Carroll et al.
2005/0203063 A1* 9/2005  Deshaies et al. ............. 514/63

OTHER PUBLICATIONS

Berkson et al., "Pilot screening programs for small molecule activators of p53", International Journal of Cancer, 115(5), 701-710, printed Jul. 10, 2005, published online on Feb. 23, 2005.*
Smith et al., Biochemical Pharmacology, vol. 23, pp. 2023-2035, 1974.*
Adams et al. (2004), "Synthesis and biological evaluation of novel curcumin analogs as anti-cancer and anti-angiogenesis agents." Bioorg. Med. Chem. 12: 3871-3883.
Altieri (2003), "Validating survivin as a cancer therapeutic target." Nat Rev Cancer 3: 46-54.
Altieri (2003), "Survivin, versatile modulation of cell division and apoptosis in cancer." Oncogene 22: 8581-8589.
Arango et al. (2003), "c-Myc overexpression sensitizes colon cancer cells to camptothecin-induced apoptosis." Br. J. Cancer 89: 1757-1765.
Arima et al. (2005), "Transcriptional blockade induces p53-dependent apoptosis associated with translocation of p53 to mitochondria." J. Biol. Chem. 280: 19166-19176.
Asada et al. (1999), "Apoptosis inhibitory activity of cytoplasmic p21(Cipl/WAFl) in monocytic differentiation." Embo. J. 18: 1223-1234.
Blagosklonny (2004), "Flavopiridol, an inhibitor of transcription: implications, problems and solutions." Cell Cycle 3: 1537-1542.
Blight et al. (2000), "Efficient initiation of HCV RNA replication in cell culture." Science 290: 1972-1974.
Boeger et al. (2005), "Structural basis of eukaryotic gene transcription." FEBS Letters 579: 899-903.
Bushnell et al. (2002), "Structural basis of transcription: alpha-amanitin-RNA polymerase II cocrystal at 2.8 A resolution." Proc. Natl. Acad. Sci. U. S. A. 99: 1218-1222.
Chafin et al. (1995), "Action of alpha-amanitin during pyrophosphorolysis and elongation by RNA polymerase II." J. Biol. Chem. 270: 19114-19119.
Chao et al. (2000), "Flavopiridol inhibits P-TEFb and blocks HIV-I replication." J. Biol. Chem. 275: 28345-28348.
Chao and Price (2001), "Flavopiridol inactivates P-TEFb and blocks most RNA polymerase II transcription in vivo." J. Biol. Chem. 216: 31793-31799.
Chattopadhyay et al. (2001), "Inactivation of p21 by EIA leads to the induction of apoptosis in DNA-damaged cells." J. Virol. 75: 9844-9856.
Chen et al. (2005), "Transcription inhibition by flavopiridol: mechanism of chronic lymphocytic leukemia cell death." Blood 106: 2513-2519.
Chipuk et al. (2003), "Pharmacologic activation of p53 elicits Bax-dependent apoptosis in the absence of transcription." Cancer Cell 4: 371-381.
Chipuk et al. (2004), "Direct activation of Bax by p53 mediates mitochondrial membrane permeabilization and apoptosis." Science 303: 1010-1014.
de Azevedo et al. (2002), "Structural basis for inhibition of cyclin-dependent kinase 9 by flavopiridol." Biochem. Biophys. Res. Comm. 293: 566-571.

(Continued)

*Primary Examiner* — Traviss C McIntosh, III
(74) *Attorney, Agent, or Firm* — McDonnell Boehnen Hulbert & Berghoff LLP

(57) ABSTRACT

The present invention provides methods of utilizing a nucleoside derivative having the chemical formula of Formula (I) to downregulate expression of an anti-apoptotic protein such as survivin in a cell, induce apoptosis in a cell, inhibit angiogenesis in a cell, inhibit binding of p53 to DNA in a cell, inhibit phosphorylation of Akt in a cell and inhibit HIV transcription in a cell, by administering to the cell or tissue an amount of a compound of Formula (I) sufficient to achieve the desired activity. Formula (I): wherein the substituents $R^a$, $R^b$, $R^c$, $R^d$, $R^e$, $R^f$, $R^g$, $R^h$, $R^i$ and $R^k$ are as defined in the specification. A particularly preferred nucleoside derivative is ARC (4-amino-6-hydrazino-7-beta-D-ribofuranosyl-7H-pyrrolo[2,3-d]-pyrimidine-5-carboxamide).

21 Claims, 10 Drawing Sheets

OTHER PUBLICATIONS

Demidenko and Blagosklonny (2004), "Flavopiridol induces p53 via initial inhibition of Mdm2 and p21 and, independently of p53, sensitizes apoptosis-reluctant cells to tumor necrosis factor." Cancer Res. 64: 3653-3660.

Deng et al. (2002), "HIV-I Tat interaction with RNA polymerase II C-terminal domain (CTD) and a dynamic association with CDK2 induce CTD phosphorylation and transcription from HIV-I promoter." J. Biol. Chem. 277: 33922-33929.

Erster et al. (2004), "In vivo mitochondrial p53 translocation triggers a rapid first wave of cell death in response to DNA damage that can precede p53 target gene activation." Mol. Cell. Biol. 24: 6728-6741.

Folkman (2004), "Endogenous angiogenesis inhibitors." APMIS 112: 496-507.

Gartel and Tyner (2002), "The role of the cyclin-dependent kinase inhibitor p21 in apoptosis." Mol. Cancer Ther. 1: 639-649.

Gartel et al. (2003), "A new method for determining the status of p53 in rumor cell lines of different origin." Oncol. Res. 13: 405-408.

Gartel and Radhakrishnan (2005), "Lost in transcription: p21 repression, mechanisms, and consequences." Cancer Res. 65: 3980-3985.

Grant and Dent (2004), "Gene profiling and the cyclin-dependent kinase inhibitor flavopiridol: what's in a name?" Mol. Cancer Ther. 3: 873-875.

Iltzsch et al. (1995), "Structure activity relationship for the binding of nucleoside ligands to adenosine kinase from Toxoplasma gondii." Biochemical Pharmacology 49(10): 1501-12.

International Search Report from International Application No. PCT/US06/15384, International Publication No. WO 2006/116512, Aug. 25, 2006.

Jack et al. (2004), "DNA—dependent protein kinase and checkpoint kinase 2 synergistically activate a latent population of p53 upon DNA damage." J. Biol Chem. 279: 15269-15273.

Janicke et al. (1998), "Caspase-3 is required for DNA fragmentation and morphological changes associated with apoptosis." J. Biol. Chem. 273: 9357-9360.

Javelaud and Besancon (2002), "Inactivation of p21WAFI sensitizes cells to apoptosis via an increase of both pI4ARF and p53 levels and an alteration of the Bax/Bcl-2 ratio." J. Biol. Chem. 277: 37949-37954.

Kaur et al. (2004), "Antiangiogenic properties of 17-(dimethylaminoethylamino)-17-demethoxygeldanamycin: an orally bioavailable heat shock protein 90 modulator." Clin. Cancer Res. 10: 4813-4821.

Kennedy et al. (1999), "Akt/Protein kinase B inhibits cell death by preventing the release of cytochrome c from mitochondria." Mol. Cell. Biol. 19: 5800-5810.

Kubbutat et al. (1997), "Regulation of p53 stability by Mdm2." Nature 387: 299-303.

Lam et al. (2001), "Genomic-scale measurement of mRNA turnover and the mechanisms of action of the anti-cancer drug flavopiridol." Genome Biol. 2: RESEARCH0041.

Lin et al. (2003), "Expression of survivin protein in human colorectal carcinogenesis." World J. Gastroenterol. 9: 974-977.

Mancebo et al. (1997), "P-TEFb kinase is required for HIV Tat transcriptional activation in vivo and in vitro." Genes Dev. 11: 2633-2644.

Marshall and Price (1995), "Purification of P-TEFb, a transcription factor required for the transition into productive elongation." J. Biol. Chem. 270: 12335-12338.

Martinou and Green (2001), "Breaking the mitochondrial barrier." Nat. Rev. Mol. Cell Biol. 2: 63-67.

Newcomb et al. (2003), "Flavopiridol induces mitochondrial-mediated apoptosis in murine glioma GL261 cells via release of cytochrome c and apoptosis inducing factor." Cell Cycle 2: 243-250.

Newcomb (2004),"Flavopiridol: pleiotropic biological effects enhance its anti-cancer activity." Anticancer Drugs 15: 411-419.

Peng (1998), "RNA polymerase II elongation control." Cold Spring Harb. Symp. Quant. Biol. 63: 365-370.

Price (2000), "P-TEFb, a cyclin-dependent kinase controlling elongation by RNA polymerase II." MoL Cell. Biol. 20: 2629-2634.

Radhakrishnan et al. (2004), "Constitutive expression of E2F-1 leads to p21 -dependent cell cycle arrest in S phase of the cell cycle." Oncogene 23: 4173-4176.

Radhakrishnan and Gartel (2005), "The PPAR-gamma agonist pioglitazone post-transcriptionally induces p21 in PC3 prostate cancer but not in other cell lines." Cell Cycle 4: 582-584.

Radhakrishnan et al. (2006), "Multiple alternate p21 transcripts are regulated by p53 in human cells." Oncogene 25 (12): 1812-5.

Radhakrishnan and Gartel (2006), "A novel transcriptional inhibitor induces apoptosis in tumor cells and exhibits antiangiogenic activity." Cancer Res. 66: 3264-70.

Radhakrishnan et al. (2007), "Proapoptotic compound ARC targets Akt and N-myc in neuroblastoma cells." Oncogene 27(5): 694-9.

Rudd and Luse (1996), "Amanitin greatly reduces the rate of transcription by RNA polymerase II ternary complexes but fails to inhibit some transcript cleavage modes." J. Biol. Chem. 271: 21549-21558.

Senderowicz (1999), "Flavopiridol: the first cyclin-dependent kinase inhibitor in human clinical trials." Invest. New Drugs 17: 313-320.

Seoane et al. (2002), "Myc suppression of the p21(Cipl) Cdlc inhibitor influences the outcome of the p53 response to DNA damage." Nature 419: 729-734.

Shilatifard et al (2003), "The RNA polymerase II elongation complex." Annu. Rev. Biochem. 72: 693-715.

Sobell (1985), "Actinomycin and DNA transcription." Proc. Natl. Acad. Sci. USA 82: 5328-5331.

Strebel (2003), "Virus-host interactions: role of HIV proteins Vif, Tat, and Rev." Aids 17 Suppl 4: S25-34.

Suzuki et al. (1998), "Resistance to Fas-mediated apoptosis: activation of caspase 3 is regulated by cell cycle regulator p21WAFI and IAP gene family ILP." Oncogene 17: 931-939.

te Poele et al. (1999), "RNA synthesis block by 5, 6-dichloro-I-beta-D-ribofuranosylbenzimidazole (DRB) triggers p53-dependent apoptosis in human colon carcinoma cells." Oncogene 18: 5765-5772.

Thompson et al. (2004), "Phosphorylation of p53 on key serines is dispensable for transcriptional activation and apoptosis." J. Biol. Chem. 279: 53015-53022.

Tian et al. (2000), "p21WAFI/CIPI antisense therapy radiosensitizes human colon cancer by converting growth arrest to apoptosis." Cancer Res. 60: 679-684.

Tishler et al. (1993), "Increases in sequence specific DNA binding by p53 following treatment with chemotherapeutic and DNA damaging agents." Cancer Res. 53: 2212-2216.

Tolman and Robins (1971), "Pyrrolopyrimidine Nucleosides: VII. A study on electrophilic and nucleophilic substitution at position six of certain pyrrolo[2,3-d]pyrimidine nucleosides." Journal of Heterocyclic Chemistry 8(5): 703-6.

Wieland and Faulstich (1991), "Fifty years of amanitin." Experientia 47: 1186-1193.

Woo et al. (1998), "DNA-dependent protein kinase acts upstream of p53 in response to DNA damage." Nature 394: 700-704.

* cited by examiner

Fig-1
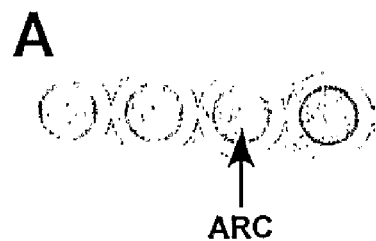
A
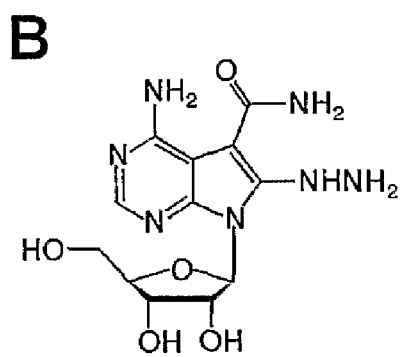
B
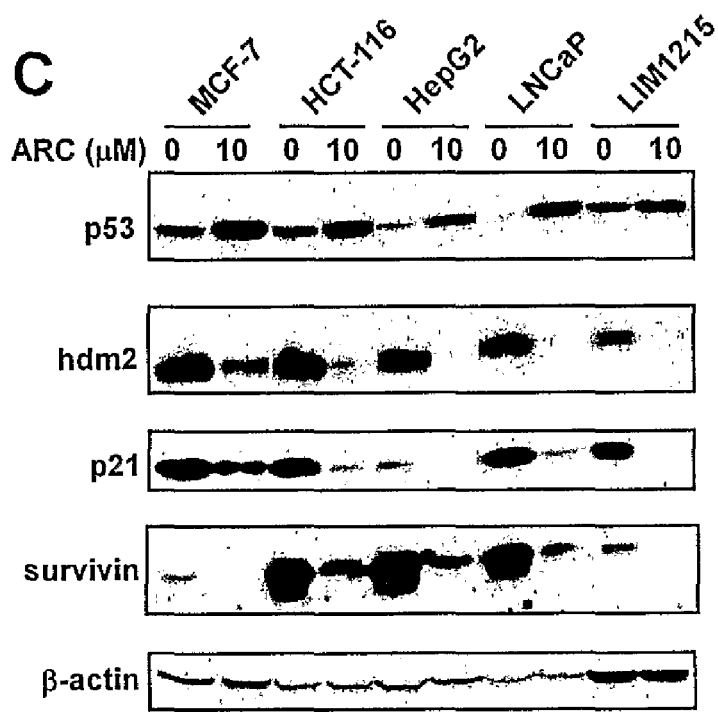
C
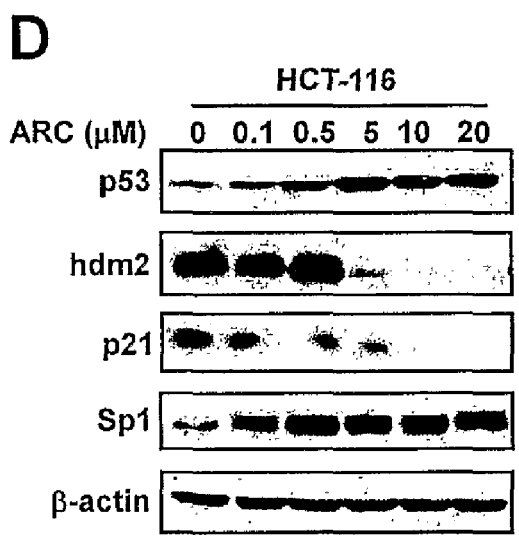
D
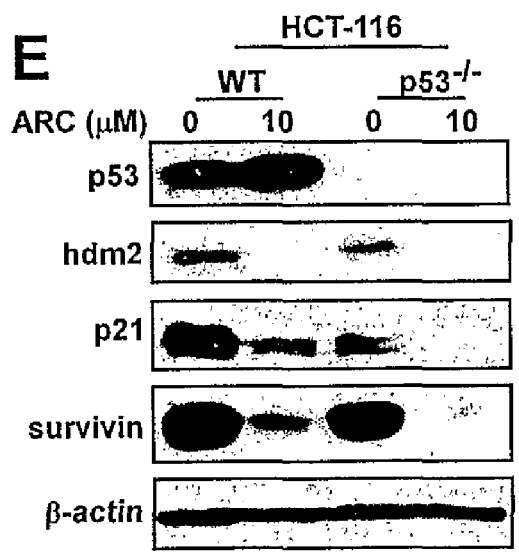
E

Fig-4
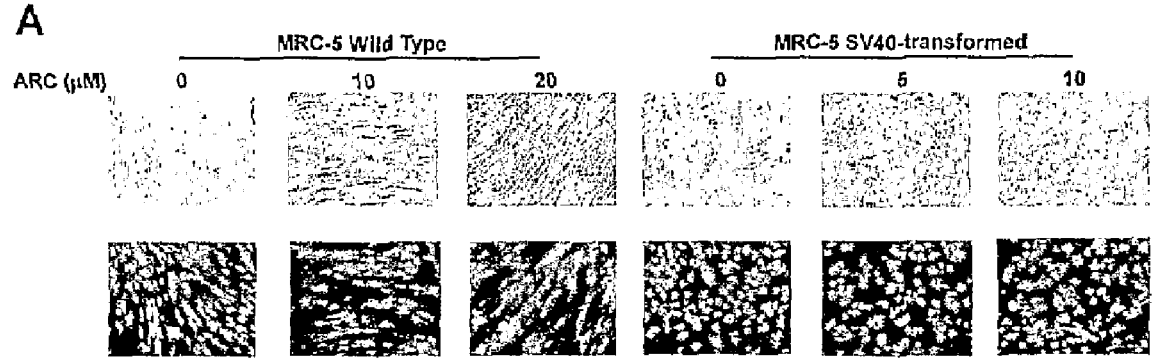
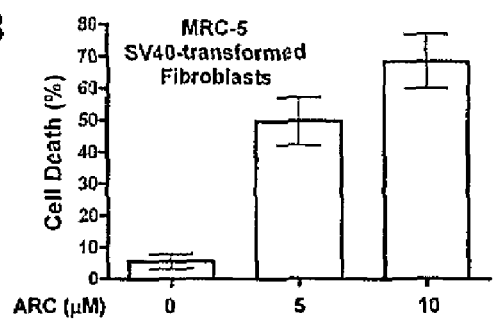
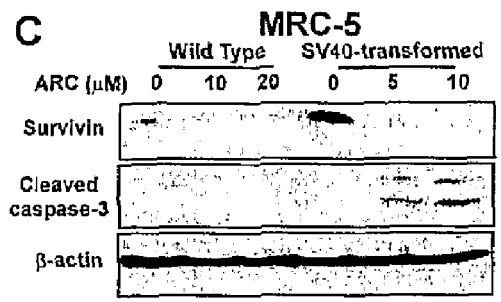
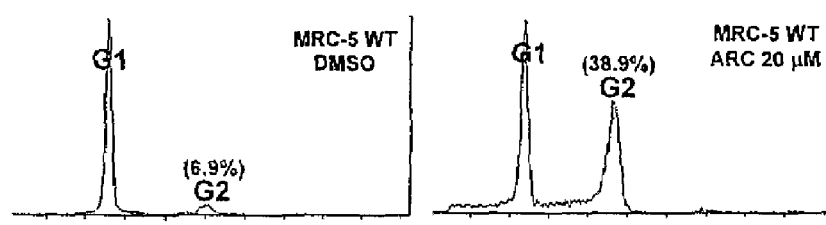

Fig-6
A
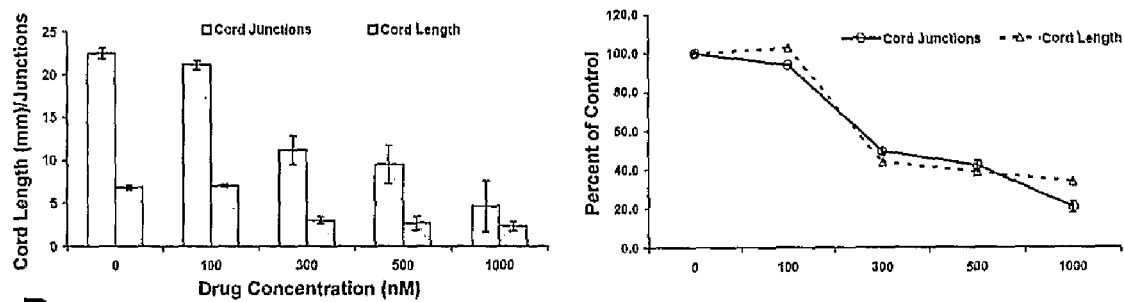
B
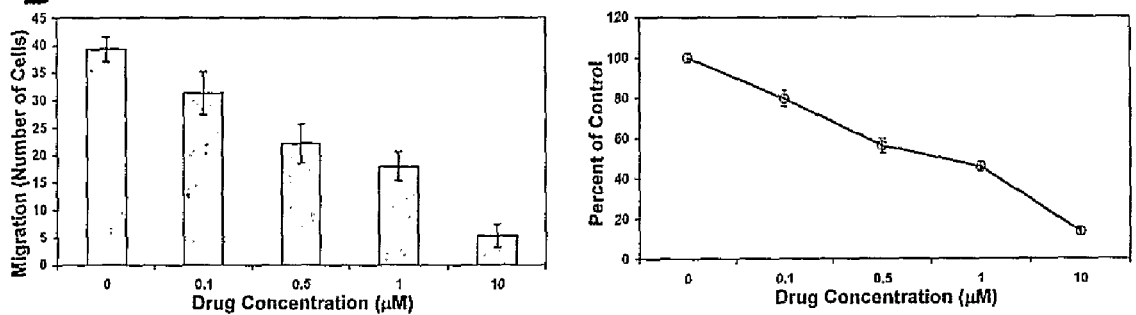
C
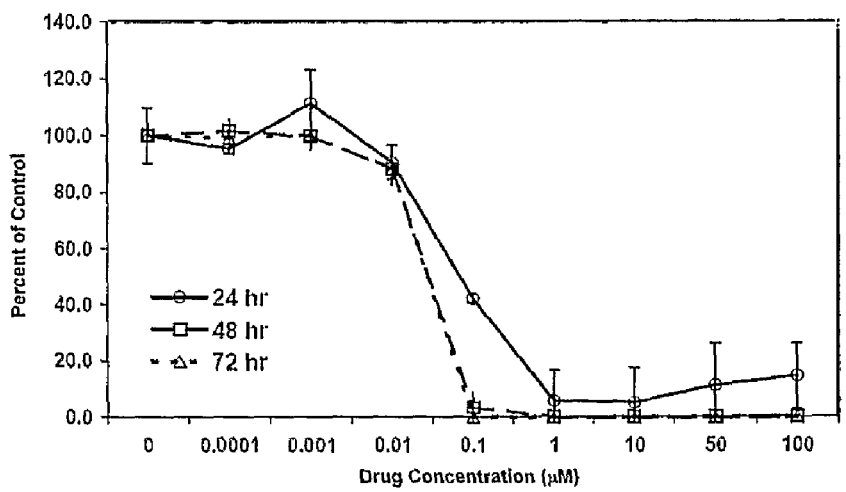

NUCLEOSIDE COMPOUNDS AND METHODS OF USE THEREOF

RELATED APPLICATIONS

The present application is a National Stage filing under 35 USC §371 of PCT Application No. PCT/US2006/015834, claiming full benefit of priority of U.S. Provisional Applications 60/674,744, filed 26 Apr. 2005, 60/703,541, filed 29 Jul. 2005, and 60/738,736, filed 22 Nov. 2005, all of which are herein incorporated by reference in their entirety.

STATEMENT OF GOVERNMENT RIGHTS

This invention was made with governmental support from the United States Government, National Institutes of Health, Grant CA91146 and the Illinois Department of Public Health, Contract No. 66280112. The United States Government and the Illinois Department of Public Health may have certain rights in the invention.

FIELD OF THE INVENTION

The invention relates to nucleoside compounds useful for inhibiting angiogenesis, inducing apoptosis in tumor cells, downregulating expression of an anti-apoptotic protein such as survivin, inhibiting p53 binding to DNA, inhibiting phosphorylation of Akt and inhibiting HIV transcription in a cell.

BACKGROUND

Cancer is recognized as the second leading cause of death worldwide. When the balance between cell proliferation and cell death is disrupted, the ensuing aberrant proliferation leads to tumor growth. Cancer treatment is still largely achieved through the use of chemo and radiotherapy, both of which cause various side-effects. Treatments which are tailored for specific tumors with minimum side-effects are the ultimate goal of cancer therapy. For certain types of tumors which express labile anti-apoptotic proteins, repression of cellular transcription could be useful. Compounds that are global transcriptional inhibitors are an attractive therapeutic option. A few examples of this class of compounds include 5,6-Dichloro-1-β-ribofuranosylbenzimidazole (DRB) and Flavopiridol.

In eukaryotes, mRNA synthesis is mediated by concerted action of a number of factors, chief among them being the RNA polymerase II [1]. The process of RNA polymerase II transcription consists of the pre-initiation, initiation and the elongation stages [2]. Several inhibitors of transcription are known, which work by blocking one or more of these stages. For example, actinomycin D, which is both a transcriptional inhibitor and a DNA damage agent, intercalates within the DNA and thus inhibits the initiation stage of transcription [3]. Flavopiridol and DRB target the elongation stage of transcription, by inhibiting positive transcription elongation factor b (P-TEFb, a cyclin-dependent protein kinase (CDK) of Cdk9/Cyclin T1) [4-6], whose phosphorylation of RNA polymerase II is essential for this stage. α-Amanitin, on the other hand, binds directly to RNA polymerase II, which leads to inhibition of both initiation and elongation stages [7-10].

General transcriptional inhibitors may be useful in cancer therapies and, in some instances, have been shown to work as anti-viral agents [11, 12]. For example, flavopiridol is a very efficient inducer of apoptosis in malignant cells and it also potentiates lethal effects of other cytotoxic drugs [11, 13]. In addition, it inhibits cell migration and displays potent anti-angiogenic activity [14, 15]. Specifically, this class of drugs may be useful against tumors that express labile anti-apoptotic proteins due to their ability to downregulate proteins of short half-life [11]. Understandably, these drugs may also act synergistically with certain factors such as tumor necrosis factor-α (TNF-α), which is known to transcriptionally induce anti-apoptotic proteins [16].

SUMMARY OF THE INVENTION

The present invention provides nucleoside derivatives having the chemical formula shown in Formula (I):

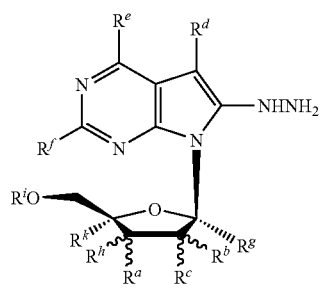

wherein $R^a$, $R^b$, $R^c$ and $R^h$ are each independently selected from the group consisting of hydrogen, cyano, azido, halogen, hydroxy, mercapto, amino, $C_{1-4}$ alkoxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms, or $R^b$ and $R^c$ together with the carbon atom to which they are attached form a 3- to 6-membered saturated monocyclic ring system optionally containing a heteroatom selected from O, S and $NC_{0-4}$ alkyl;

$R^d$ is hydrogen, cyano, nitro, $C_{1-3}$ alkyl, $NHCONH_2$, $CONR^jR^j$, $CSNR^jR^j$, $COOR^j$, $C(=NH)NH_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl) or (imidazol-2-yl), wherein alkyl is unsubstituted or substituted with one to three groups independently selected from halogen, amino, hydroxy, carboxy and $C_{1-3}$ alkoxy;

$R^e$ and $R^f$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino or $C_{4-6}$ cycloheteroalkyl, unsubstituted or substituted with one to two groups independently selected from halogen, hydroxy, amino, $C_{1-4}$ alkyl and $C_{1-4}$ alkoxy;

$R^i$ is hydrogen, $C_{1-10}$ alkylcarbonyl, $P_3O_9H_4$, $P_2O_6H_3$ or $P(O)R^mR^n$;

each $R^j$ is independently hydrogen or $C_{1-6}$ alkyl;

$R^k$ and $R^g$ are each independently hydrogen, methyl, hydroxymethyl or fluoromethyl; and $R^m$ and $R^n$ are each independently hydroxy, $OCH_2CH_2SC(=O)C_{1-4}$ alkyl, $OCH_2O(C=O)OC_{1-4}$ alkyl, $NHCHMeCO_2Me$, $OCH(C_{1-4}$ alkyl)$O(C=O)C_{1-4}$ alkyl, wherein alkyl is unsubstituted or substituted with one to three groups independently selected from halogen, amino, hydroxy, carboxy and $C_{1-3}$ alkoxy.

A particularly preferred nucleoside derivative of the invention is a compound having the chemical formula of Formula (II):

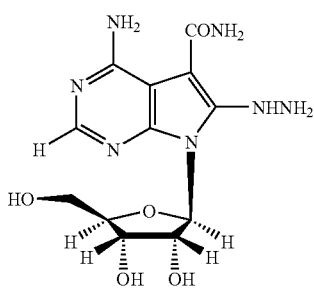

which has the chemical name: 4-amino-6-hydrazino-7-beta-D-ribofuranosyl-7H-pyrrolo[2, 3-d]-pyrimidine-5-carboxamide, and is referred to herein as ARC.

The nucleoside derivatives of the invention are useful for inhibiting angiogenesis, inducing apoptosis in tumor cells, downregulating expression of an anti-apoptotic protein such as survivin, inhibiting p53 binding to DNA, inhibiting phosphorylation of Akt, as well as for inhibiting transcription, and inhibiting tumor growth.

ARC acts as a general inhibitor of transcription and promotes apoptosis in several human cancer cell lines including MCF-7 breast cancer, LIM1215 colon cancer, AGS gastric cancer and HepG2 liver cancer cells. This compound increases p53 levels, but represses the expression of key p53 targets p21 and hdm2 in cancer cell lines. In addition, ARC downregulates survivin, a target of repression by p53, and inhibits the DNA-binding ability of p53. However, repressions of various genes by ARC were found to be p53-independent, and likely due to the combined effect of general transcriptional repression by ARC and short half-life of these proteins. In line with its ability to induce potent apoptosis in cancer cells, ARC could be useful as a therapeutic agent in treatment of certain types of cancer and also as a reagent for studying gene transcription.

The nucleoside derivatives of Formula (I), such as ARC, inhibit phosphorylation of RNA polymerase II by P-TEFb (positive transcription elongation factor b) leading to a block in transcriptional elongation. In addition, the nucleoside derivatives inhibit phosphorylation of p53 by P-TEFb, which is required for p53 DNA binding activity. Remarkably, the nucleoside derivatives of Formula (I) such as ARC, induce potent apoptosis in human tumor and transformed cells, but not in normal cells, and exhibit strong anti-angiogenic activity in vitro. Cell death induced by ARC was strongly correlated with downregulation of the anti-apoptotic gene survivin, which is overexpressed in majority of human tumors. Accordingly, nucleoside derivatives of Formula (I) provide a therapeutic agent for treatment of cancer and related diseases.

Accordingly, the present invention provides a method of downregulating expression of an anti-apoptotic protein, such as survivin in a cell. The method comprises administering an anti-apoptotic protein expression downregulating amount of a nucleoside derivative of Formula (I) (e.g. ARC) to a cell that expresses the anti-apoptotic protein.

The present invention also provides a method of inducing apoptosis in a tumor cell involving administering an apoptosis-inducing amount of a nucleoside derivative of Formula (I) to a tumor cell. Preferably, the nucleoside derivative is ARC.

In another aspect, the present invention provides a method of inhibiting angiogenesis in a tissue. The method comprises administering an anti-angiogenic amount of a nucleoside derivative of Formula (I) to a tissue undergoing angiogenesis. A preferred nucleoside derivative is ARC.

In yet another aspect, the present invention provides a method of inhibiting p53 binding to DNA in a cell. This method comprises contacting a cell with an amount of nucleoside derivative of Formula (I), such as ARC, sufficient to inhibit binding of p53 to DNA in the cell.

In a further aspect, the present invention provides a method of inhibiting phosphorylation of Akt in a cell. The method comprises contacting a cell with an amount of a nucleoside derivative of Formula (I), such as ARC, sufficient to inhibit phosphorylation of Akt in the cell.

In addition, the present invention provides a method of inhibiting HIV transcription in a cell comprising contacting a cell with an amount of a nucleoside derivative of Formula (I) sufficient to inhibit HIV transcription in the cell.

BRIEF DESCRIPTION OF THE DRAWINGS

FIG. 1. Identification of ARC. (A) Screening of the NCI diversity set of ~2000 compounds in LIM1215 cells containing lacZ under the control of p21 promoter. Compounds were used at a final concentration of 10 μM. Part of the 96-well plate containing ARC is shown. (B) Chemical structure of ARC (4-Amino-6-hydrazino-7-beta-D-Ribofuranosyl-7H-Pyrrolo[2,3-d]-pyrimidine-5-Carboxamide). (C) Cancer cell lines of different origin were treated either with DMSO (dimethyl sulfoxide) control or 10 μM of ARC for 24 hours and subjected to immunoblotting with the indicated antibodies. (D) HCT-116 colon cancer cells were treated with increasing amounts of ARC for 24 hours and cell lysates were analyzed for the levels of indicated proteins. (E) Wild-type HCT-116 and HCT-116-p53$^{-/-}$ cells were treated with either DMSO or ARC and the cell lysates were used for immunoblotting as indicated.

FIG. 4. ARC-mediated apoptosis is specific for transformed cell type. (A) Wild type and SV40-transformed MRC-5 human fetal lung fibroblasts were treated with indicated concentrations of ARC for 24 hours. Photographs from phase contrast microscopy (top panel) and fluorescent microscopy after DAPI (4',6-diamidino-2-phenylindole) staining (bottom panel) are shown. (B) Apoptotic nuclei from SV40-transformed MRC-5 fibroblasts treated with indicated concentrations of ARC for 24 hours were scored after DAPI staining and percentage cell death (mean±sd; n=3) is shown. (C) Wild type and SV40-transformed MRC-5 fibroblasts were treated with ARC as indicated for 24 hours and the cell lysates were used for immunoblotting and probed for levels of survivin and cleaved caspase-3. (D) Wild type MRC-5 fibroblasts were treated either with DMSO or 20 μM of ARC for 48 hours and analyzed by flow cytometry after propidium iodide staining.

FIG. 6. ARC acts as a potent anti-angiogenic agent in vitro. (A) HUVECs (human umbilical vein endothelial cells) were treated with different concentrations of ARC as indicated for 24 hours and cord formation was assessed by cord junctions and cord length. The right panel indicates the same data in terms of percentage. (B) Motility assay was performed with HUVECs pretreated with indicated concentrations of ARC and with Vascular Endothilial Growth Factor (VEGF) as chemoattractant. The right panel represents the same data in terms of percentage. (C) HUVECs were used in the proliferation assay with different concentrations of ARC as indicated for different time points (24, 48 and 72 hours).

DETAILED DESCRIPTION OF PREFERRED EMBODIMENTS

Figure 2:
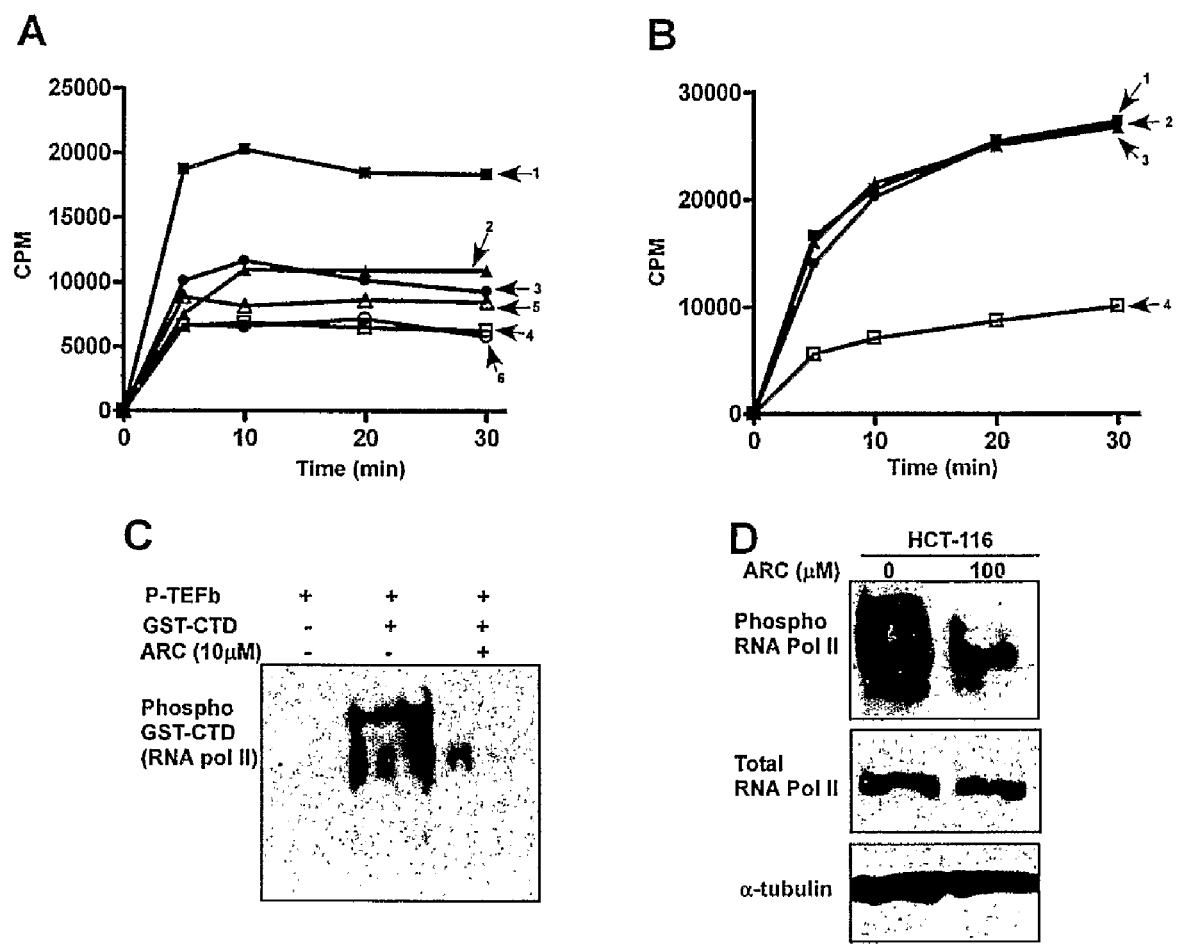
FIG. 2. ARC is a general transcription inhibitor affecting RNA polymerase II transcription. (A) Nuclei were isolated from HCT-116 colon cancer cells treated for 2 hours with one of DMSO, 1 mM ARC, or 1 mM DRB. The nuclei were assayed for rate of transcription (DMSO—curve 1; ARC—curve 2; DRB—curve 3) as described herein. The same nuclei were also assayed for transcription rate in the presence of 2 μg/ml of α-amanitin (DMSO—curve 4; ARC—curve 5; DRB—curve 6). (B) Nuclei were isolated from untreated HCT-116 cells. These nuclei were then treated with one of DMSO (curve 1), 50 μM ARC (curve 2), 50 μM DRB (curve 3), or 2 μg/ml α-amanitin (curve 4) and used in the nuclear run-on assay. (C) Purified P-TEFb was used for kinase assays with GST-CTD (GST-tagged C-terminal domain of RNA polymerase II) as a substrate either in the presence or absence of ARC as indicated. The extent of CTD (C-terminal domain) phosphorylation was determined by immunoblotting using anti-phospho-RNA polymerase II antibodies. (D) HCT-116 cells were treated with the indicated concentrations of ARC for 3 hours and total cell lysates were probed for the levels of phospho-RNA polymerase II, total RNA polymerase II and x-tubulin.

The present invention provides nucleoside derivatives having the chemical formula shown in Formula (I):

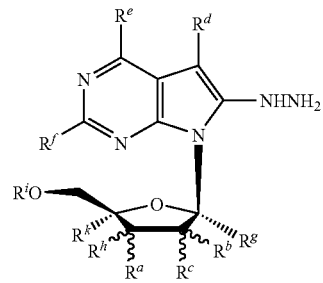

wherein $R^a$, $R^b$, $R^c$ and $R^h$ are each independently selected from the group consisting of hydrogen, cyano, azido, halogen, hydroxy, mercapto, amino, $C_{1-4}$ alkoxy, $C_{2-4}$ alkenyl, $C_{2-4}$ alkynyl and $C_{1-4}$ alkyl, wherein alkyl is unsubstituted or substituted with hydroxy, amino, $C_{1-4}$ alkoxy, $C_4$ alkylthio, or one to three fluorine atoms, or $R^b$ and $R^c$ together with the carbon atom to which they are attached form a 3- to 6-membered saturated monocyclic ring system optionally containing a heteroatom selected from O, S and $NC_{0-4}$ alkyl;

$R^d$ is hydrogen, cyano, nitro, $C_{1-3}$ allyl, $NHCONH_2$, $CONR^jR^j$, $CSNR^jR^j$, $COOR^j$, $C(=NH)NH_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl) or (imidazol-2-yl) wherein alkyl is unsubstituted or substituted with one to three groups independently selected from halogen, amino, hydroxy, carboxy and $C_{1-3}$ alkoxy;

$R^e$ and $R^f$ are each independently hydrogen, hydroxy, halogen, $C_{1-4}$ alkoxy, amino, $C_{1-4}$ alkylamino, di($C_{1-4}$ alkyl) amino, $C_{3-6}$ cycloalkylamino, di($C_{3-6}$ cycloalkyl)amino, or $C_{4-6}$ cycloheteroalkyl, unsubstituted or substituted with one to two groups independently selected from halogen, hydroxy, amino, $C_{1-4}$ alkyl and $C_{1-4}$ alkoxy;

$R^i$ is hydrogen, $C_{1-10}$ alkylcarbonyl, $P_3O_9H_4$, $P_2O_6H_3$ or $P(O)R^mR^n$;

each $R^j$ is independently hydrogen or $C_{1-6}$ alkyl;

$R^k$ and $R^g$ are each independently hydrogen, methyl, hydroxymethyl or fluoromethyl; and R′′′ and R′′′′ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl, wherein alkyl is unsubstituted or substituted with one to three groups independently selected from halogen, amino, hydroxy, carboxy and C$_{1-3}$ alkoxy. Me is methyl.

The nucleoside derivatives of Formula (I) can be prepared using established methods including the synthetic methods described in "Chemistry of Nucleosides and Nucleotides," L. B. Townsend, ed., Vols. 1-3, Plenum Press (1988), which is incorporated by reference. Additional synthetic methods are described in Carroll et al., U.S. Publication No. US2004/0110717 published Jun. 10, 2004 and methods for the formation of hydrazine-containing compounds are described in J. March, "Advanced Organic Chemistry," Fourth Edition, John Wiley & Sons (1992), both of which are incorporated by reference.

The nucleoside derivatives of the invention can be in neutral form or in the form of a salt, preferably a physiologically acceptable salt (e.g., a mineral acid salt). In a preferred embodiment, R$^d$ is CONH$_2$. In another preferred embodiment, R$^e$ is NH$_2$ and R$^f$ is H. In yet another preferred embodiment, R$^a$ and R$^c$ are each hydroxy, and R$^b$, R$^g$, R$^h$, and R$^i$ are each H. Most preferably, the nucleoside derivative is ARC (4-amino-6-hydrazino-7-beta-D-ribofuranosyl-7H-pyrrolo[2,3-d]-pyrimidine-5-carboxamide), Formula (II).

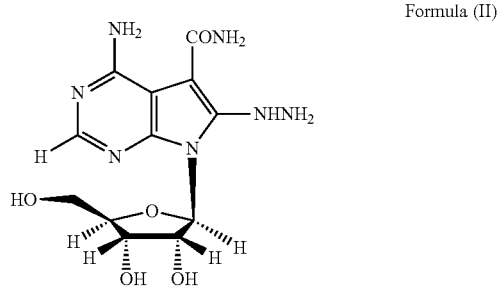

Formula (II)

The present invention provides a method of downregulating survivin (or anti-apoptotic protein) expression in a cell. Survivin is an anti-apoptotic protein that protects cells from apoptosis. One method comprises administering a survivin expression down-regulating amount of a nucleoside derivative of Formula (I) (e.g. ARC) to a survivin expressing cell. As used herein, the phrase "a survivin expression downregulating amount" or "survivin expression inhibiting amount" means an amount of a nucleoside derivative of Formula (I) that will provide a desired level of survivin expression suppression in cells of a selected cell line. In a similar manner, the phrase "an anti-apoptotic protein expression downregulating amount" or "an anti-apoptotic protein expression inhibiting amount" means an amount of a nucleoside derivative of Formula (I) that will provide a desired level of anti-apoptotic protein expression suppression in cells of a selected cell line. The amount of nucleoside analog to be administered to achieve the desired level of suppression of survivin (or anti-apoptotic protein) expression can be readily determined by one of ordinary skill in the art utilizing any assay suitable for evaluating survivin (or anti-apoptotic protein) expression, such as the assays described herein and in the references cited herein. Preferably, the cell is a human cell, more preferably a tumor cell, such as a human tumor cell.

The present invention also provides a method of inducing apoptosis in a tumor cell involving administering an apoptosis-inducing amount of a nucleoside derivative of Formula (I) to a tumor cell. Preferably, the nucleoside derivative is ARC. As used herein, the phrase "an apoptosis-inducing amount" means an amount of a nucleoside derivative of Formula (I) that will induce a desired level of apoptosis in cells of a selected cell line. The amount of nucleoside analog to be administered to achieve the desired level of apoptosis can be readily determined by one of ordinary skill in the art utilizing any apoptosis assay, such as the apoptosis assays described herein and in the references cited herein. Preferably, the cell is a human cell.

In another aspect, the present invention provides a method of inhibiting angiogenesis in a tissue. The method comprises administering an anti-angiogenic amount of a nucleoside derivative of Formula (I) to a tissue undergoing angiogenesis. A preferred nucleoside derivative is ARC. As used herein, the phrase "an anti-angiogenic amount" means an amount of a nucleoside derivative of Formula (I) that will provide a desired level of angiogenesis suppression in cells of a selected cell line. The amount of nucleoside analog to be administered to achieve the desired level of angiogenesis suppression can be readily determined by one of ordinary skill in the art utilizing any angiogenesis assay, such as the angiogenesis assays described herein and in the references cited herein. Preferably, the tissue is a human tissue, more preferably a tumor, such as a human tumor.

In yet another aspect, the present invention provides a method of inhibiting p53 binding to DNA in a cell. This method comprises contacting a cell with an amount of nucleoside derivative of Formula (I), such as ARC, sufficient to inhibit binding of p53 to DNA in the cell. As used herein, the phrase "an amount of nucleoside derivative of Formula (I), such as ARC, sufficient to inhibit binding of p53 to DNA in the cell" means an amount of a nucleoside derivative of Formula (I) that will provide a desired level of p53-DNA-binding suppression in cells of a selected cell line. The amount of nucleoside analog to be administered to achieve the desired level of binding inhibition can be readily determined by one of ordinary skill in the art utilizing any assay suitable for evaluating p53 binding to DNA, such as the assays described herein and in the references cited herein. Preferably, the cell is a human cell, more preferably a tumor cell, such as a human tumor cell.

In a further aspect, the present invention provides a method of inhibiting phosphorylation of Akt in a cell. This method comprises contacting a cell with an amount of a nucleoside derivative of Formula (I), such as ARC, sufficient to inhibit phosphorylation of Akt in the cell. As used herein, the phrase "an amount of nucleoside derivative of Formula (I), such as ARC, sufficient to inhibit phosphorylation in the cell" means an amount of a nucleoside derivative of Formula (I) that will provide a desired level of Akt phosphorylation inhibition in cells of a selected cell line. The amount of nucleoside analog to be administered to achieve the desired level of phosphorylation inhibition can be readily determined by one of ordinary skill in the art using any assay suitable for evaluating phosphorylation, such as the assays described herein and in the references cited herein. Preferably, the cell is a human cell, more preferably a tumor cell, such as a human tumor cell.

In addition, the present invention provides a method of inhibiting HIV transcription in a cell comprising contacting a cell with an amount of a nucleoside derivative of Formula (I) sufficient to inhibit HIV transcription in the cell. As used herein, the phrase "an amount of nucleoside derivative of Formula (I), such as ARC, sufficient to inhibit HIV transcription in the cell" means an amount of a nucleoside derivative of Formula (I) that will provide a desired level of transcription inhibition in cells of a selected cell line. The amount of nucleoside analog to be administered to achieve the desired level of transcription inhibition can be readily determined by one of ordinary skill in the art using any assay suitable for evaluating transcription, such as the assays described herein and in the references cited herein. Preferably, the cell is a human cell.

All references referred to or cited herein are incorporated herein by reference.

The following Examples are provided to further illustrate preferred embodiments of the present invention and are not to be construed as limiting the scope of the invention.

PROCEDURES AND EXAMPLES

Cell Lines and Media

Colon cancer LIM1215, breast cancer MCF-7, liver cancer HepG2, gastric cancer AGS and prostate cancer LNCaP cells were obtained from ATCC. Wild type and SV40-transformed MRC-5 human fetal lung fibroblasts were obtained from Coriell Institute. Isogenic colon cancer HCT-116 wild-type and p53$^{-/-}$ cell lines were a kind gift from Dr. Vogelstein (Johns Hopkins University). MCF-7 and HepG2 cells with stable knock-down of p53 (MCF-7-p53si and HepG2-p53si, respectively) have been described previously [26]. The cells were grown in different media as described [47].

High Throughput Screening of Chemical Library

LIM1215 colon carcinoma cells harboring the lacZ reporter gene under the control of a 2.3 kb p21 promoter (containing two p53 binding sites) were grown in 96-well plates. Diversity set, a chemical compound library containing approximately 2000 compounds (dissolved in DMSO), was obtained from the National Cancer Institute (NCI) and was used at a final concentration of 10 µM on the cells for 24 hours. lacZ encoded β-Gal was detected by X-Gal staining as described previously [48].

Immunoblot Analysis

Immunoblotting was performed as described [49] with antibodies specific for p53 (sc-126 HRP; Santa Cruz), hdm2 (sc-965; Santa Cruz), p21 (556431; BD Pharmingen), Sp1 (sc-59; Santa Cruz), survivin (sc-10811; Santa Cruz), phospho RNA polymerase II (4735; Cell Signaling), total RNA polymerase II (8WG16; a gift from Dr. Schlegel, University of Illinois at Chicago), α-tubulin (T9026; Sigma), cleaved caspase-3 (9664; Cell Signaling), caspase-9 (9502; Cell Signaling) and β-actin (A5441; Sigma) antibodies.

Nuclear Run-on Assay

Run-on assays with isolated nuclei were performed as described [4]. Briefly, cells treated with the indicated agents were lysed with hypotonic buffer (10 mM Tris-HCl pH 7.4, 10 mM NaCl and 35 mM MgCl$_2$) and nuclei collected by centrifugation and resuspended in nuclear storage buffer (50 mM HEPES pH 8.0, 5 mM MgCl$_2$, 0.5 mM DTT, 1 mg/ml BSA and 25% (v/v) glycerol) at about 5×10$^8$ nuclei/ml and stored at −80° C. Transcription reactions were performed in 200 µl volume consisting of 1×10$^7$ nuclei in the presence of 0.12 M KCl, 7 mM Mg(Ac)$_2$, 25 µCi of [$^{32}$P]GTP, 500 µM ATP, UTP and CTP at 30° C. Samples were collected at various time points (18 µl/time point—0, 5, 10, 20 and 30 min) and the reaction terminated by the addition of 57 µl of Sarkosyl solution (1% Sarkosyl, 0.1 M Tris pH 8.0, 0.1 M NaCl, 10 mM EDTA and 200 µg/ml tRNA). The stopped reactions were transferred to Whatman DE81 paper, and washed four times with wash buffer (5% K$_2$HPO$_4$ and 0.3% Na$_4$P$_2$O$_7$) for 10 min, followed by a 5-min water wash. Then the paper was briefly rinsed with 95% ethanol and allowed to dry completely. Radiation was quantitated using a liquid scintillation counter.

Kinase Assays

Purified P-TEFb (Cdk9/Cyclin T1) protein and GST-CTD (GST-tagged C-terminal domain of RNA polymerase II) expression plasmid were gifts from Dr. Nekhai (Howard University). GST-CTD protein was expressed in BL21 E. coli (Stratagene) and purified using a GST protein purification kit (Amersham Biosciences). The kinase assay was performed at 30° C. for 1 hour in the presence of P-TEFb with or without the addition of ARC. The phosphorylation levels of GST-CTD were detected with anti-phospho RNA polymerase II antibody (4735; Cell Signaling).

For P-TEFb kinase assays with p53 as a substrate, purified p53 protein (Protein One) was used. Twenty-five nanograms of p53 protein along with [γ$^{32}$P]ATP was used in reactions either in the presence or absence of P-TEFb, with or without the addition of ARC. The reaction was carried out at 30° C. for 30 min. The samples were resolved on an SDS-PAGE and transferred on to a PVDF membrane and exposed to X-ray film to detect phosphorylation of p53.

Gel Shift Assay

Either purified p53 protein or nuclear extracts were used in the gel shift assays. For preparation of nuclear extracts, cells treated either with DMSO or different agents (doxorubicin, ARC and actinomycin D) were harvested 24 hours later and lysed in hypotonic buffer (10 mM HEPES pH 7.9, 1.5 mM MgCl$_2$, 10 mM KCl, 0.2 mM PMSF, 0.5 mM DTT, 1 mM Na$_3$VO$_4$, 1 mM NaF, 1 mM Aprotinin and 1 mM Leupeptin), nuclei pelleted and treated with high-salt buffer (20 mM HEPES pH 7.9, 20% (v/v) glycerol, 1.5 mM MgCl$_2$, 0.5 M KCl, 0.2 mM EDTA, 0.2 mM PMSF, 0.5 mM DTT, 1 mM Na$_3$VO4, 1 mM NaF, 1 mM Aprotinin and 1 mM Leupeptin). Nuclear extracts (10 µg) or purified p53 protein (100 ng) were incubated with 0.5 ng of p53 consensus double-stranded oligos (5'-TAC AGA ACA TGT CTA AGC ATG CTG GGG ACT-3'; Santa Cruz Biotechnology) that were labeled with [γ$^{32}$P]ATP. As a control, anti-p53 antibody (PAb421, EMD Biosciences) was used to supershift the p53/DNA complex. The reaction mixtures were resolved on a 4% acrylamide DNA-retardation gel, dried and exposed to X-ray film in the presence of intensifying screen.

Apoptosis Assays

Apoptosis was detected either by DAPI (4',6-diamidino-2-phenylindole) staining or by Flow Cytometry after PI (Propidium Iodide) staining. For DAPI staining, all treatments (DMSO or ARC) were done in triplicates in 6-well plates and cells were stained with DAPI and visualized by fluorescent microscopy. Four random fields for each sample were photographed and at least 500 cells per field were counted to estimate apoptosis. The data is represented as mean±Standard deviation (sd).

For Flow Cytometry, cells were fixed in 70% ethanol and stored at −20° C. until further analysis. Equal numbers of fixed cells were then stained with PI solution (0.1% Triton X-100, 0.2 mg/ml DNase free RNase, 0.02 mg/ml propidium iodide) made in PBS for 15 min at 37° C. and analyzed by a flow cytometer.

Angiogenesis Assays

Different angiogenesis assays such as cord formation assay, motility assay and proliferation inhibition assay were performed at the developmental therapeutics program (DTP) branch of NCI (NCI/DTP) as described [50]. HUVECs were used for all the assays. Taxol and TNP-470 were used as positive control for the assays.

Example 1

A Novel Compound ARC Represses p53 Targets but Increases p53 Levels

Recent studies have demonstrated that blocking the function of p21 enhances apoptosis of cancer cells [17-21], which could be beneficial in cancer therapy. In order to find small molecule transcriptional inhibitors of p21, we generated LIM1215 colon cancer cells, carrying lacZ under the control of p21 promoter, as a screening system for testing ~2000 structurally diverse compounds (Diversity Set) obtained from National Cancer Institute (NCI). Out of the five compounds that were able to repress the p21 promoter (judged on their ability to attenuate p21 promoter driven β-Gal expression), the most potent one was selected for detailed characterization. The ability of the compound, which we named ARC (4-Amino-6-hydrazino-7-beta-D-Ribofuranosyl-7H-Pyrrolo [2,3-d]-pyrimidine-5-Carboxamide; NSC-188491) to inhibit p21 promoter is illustrated in a sample of the screen (FIG. 1A). ARC is a nucleoside analog (FIG. 1B), and was able to repress p21 levels in a variety of cell lines derived from cancers of different origin (FIG. 1C). In addition, ARC was able to downregulate hdm2 (an induced target of p53) and survivin (a repressed target of p53), although it increased p53 levels (FIG. 1C). To determine if these effects mediated by ARC were dose-dependent, we treated HCT-116 colon carcinoma cells with different concentrations of ARC. We found that ARC increased p53 but simultaneously repressed its target genes p21 and hdm2 in a dose-dependent manner, while no significant changes were observed in Sp1 and β-actin levels (FIG. 1D).

In order to evaluate the extent to which the ARC-mediated repression of p21, hdm2 and survivin are p53-dependent, a pair of isogenic colon cancer cell lines was employed differing only in their p53 status—HCT-116 wild-type and HCT-116-p53$^{-/-}$ cells (gift from Dr. Bert Vogelstein). Comparison of the p21, hdm2 and survivin levels in HCT-116-p53$^{+/+}$ and HCT-116-p53$^{-/-}$ before and after treatment with ARC revealed that these genes are repressed irrespective of their p53 status (FIG. 1E) implying that ARC operates through a p53-independent mechanism.

Example 2

ARC is a General Transcriptional Inhibitor that Functions by Inhibiting RNA Polymerase II Phosphorylation Some transcriptional inhibitors such as DRB and flavopiridol repress p21 and hdm2 while increasing p53 levels [4, 16]. ARC displays a similar pattern, indicating that it acts as a global transcriptional inhibitor. To evaluate this activity, HCT-116 cells were treated with one of DMSO (control), ARC or DRB, and nuclei were isolated. These nuclei were assayed for rate of transcription either in the presence or absence of α-amanitin using the nuclear run-on assay. It was found that the rates of transcription were lower in nuclei treated with ARC and DRB than the control nuclei (FIG. 2A), clearly demonstrating that ARC can act as an inhibitor at the level of transcription. It is known that α-amanitin inhibits RNA polymerase II, but does not affect RNA polymerase I and III based transcription. If ARC inhibits polymerase I and III transcription, the rate of transcription should be substantially lower in the ARC+α-amanitin (FIG. 2A; curve 5) when compared with DMSO+α-amanitin (FIG. 2A; curve 4). However both of these rates of transcription were similar, implying that ARC might preferentially affect only RNA polymerase II transcription.

In order to evaluate the ability of ARC to bind to and inhibit RNA polymerase II directly (like α-amanitin) or indirectly (like DRB), nuclei were isolated from normally growing untreated HCT-116 cells and treated with each of these agents, and then assayed for rate of transcription by nuclear run-on assay. The addition of DRB or ARC did not affect the rate of transcription, while α-amanitin addition dramatically inhibited transcription (FIG. 2B), implying that ARC affects polymerase II transcription in an indirect manner It is known that DRB and flavopiridol inhibit transcription by blocking the kinase activity of P-TEFb, which in turn leads to decreased phosphorylation of RNA polymerase II C-terminal domain (CTD) [4]. To determine if ARC operates by a similar mechanism, a kinase assay was performed with purified P-TEFb using GST-CTD (GST tagged C-terminal domain of RNA polymerase II) as the substrate. Addition of ARC potently decreased the phosphorylation of GST-CTD (FIG. 2C), suggesting that ARC can inhibit P-TEFb kinase activity. To evaluate this effect in vivo, HCT-116 cells were treated with ARC for 3 hours and analyzed levels of phospho-RNA polymerase II by immunoblotting. While the total amount of RNA polymerase II remained unchanged, phosphorylation of the RNA polymerase II CTD decreased upon ARC treatment (FIG. 2D), consistent with the in vitro kinase assay.

Example 3

Figure 3:
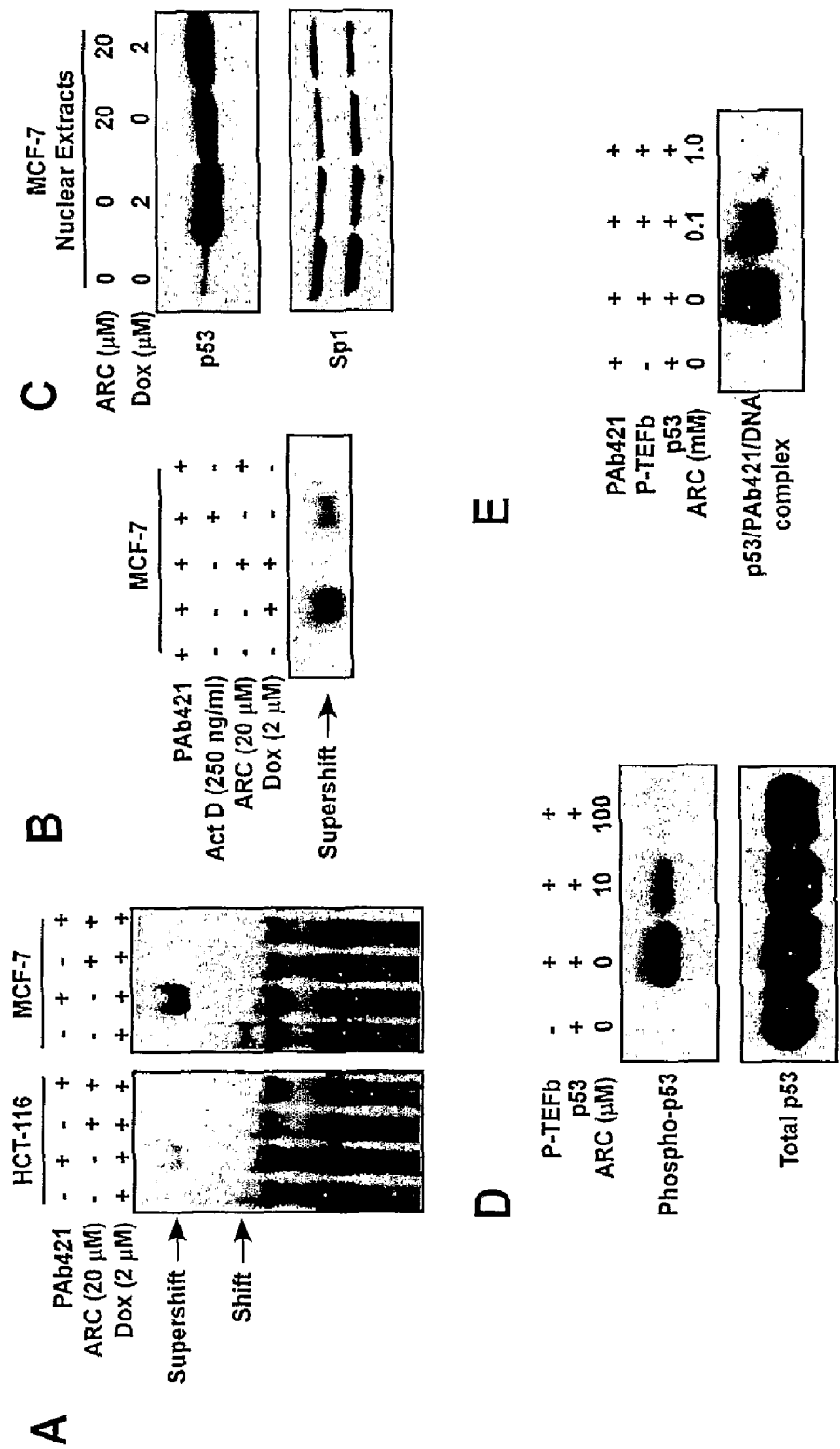
FIG. 3. ARC inhibits DNA binding ability of p53 and phosphorylation of p53 by P-TEFb. (A) Nuclear extracts from HCT-116 and MCF-7 cells treated with indicated concentrations of Doxorubicin (Dox) and ARC were subjected to gel shift assay with a radio-labeled p53 consensus probe. The anti-p53 antibody PAb421 was used for supershifting the DNA-protein complexes. (B) MCF-7 cells were treated with different combinations of doxonibicin (Dox), actinomycin D (Act D), or ARC as indicated and nuclear extracts were used in gel shift assay with p53 consensus probe. Only the supershifted bands with the anti-p53 antibody PAb421 are shown. (C) Nuclear extracts from MCF-7 cells treated as indicated were subjected immunoblotting with anti-p53 and anti-Sp1 antibodies. (D) In vitro kinase assay was performed to assess the ability of P-TEFb kinase to phosphorylate p53 and to investigate if ARC can inhibit this phosphorylation. (E) Purified p53 protein was used in gel shift reactions with or without phosphorylation by P-TEFb. Different concentrations of ARC were added as indicated. Only the supershifted bands with PAb421 are shown.

ARC Inhibits DNA Binding Ability of p53 and Phosphorylation of p53 by P-TEFb Although the effects of ARC were p53-independent, ARC did affect some properties of p53. It was observed that ARC inhibited the doxorubicin-induced DNA binding ability of p53 to its consensus sequence, as determined from the nuclear extracts derived from HCT-116 and MCF-7 cells (FIGS. 3A and 3B). This is in contrast to actinomycin D, which is known to enhance the DNA binding ability of p53 [22]. ARC treatment alone did not influence the DNA binding ability of p53, but treatment of cells with actinomycin D increased the DNA binding ability of p53 as expected (FIG. 3B). To determine if ARC retains p53 in the cytoplasm, which may lead to decreased binding in the gel shift assays, p53 levels in nuclear lysates were examined. Levels of p53 in the nuclear extracts after treatment with doxorubicin+ARC did not change significantly when compared with the levels from sample treated with doxorubicin alone (FIG. 3C). Also, p53 was highly induced in nuclear extracts derived from cells treated with ARC alone (FIG. 3C), clearly indicating that ARC does not modulate p53 by nuclear exclusion.

Since post-translational modifications, especially phosphorylation, play an important role in the DNA binding ability of p53 after DNA damage [23, 24], this indicates that p53 is a substrate for P-TEFb kinase and that ARC-mediated inhibition of p53 phosphorylation by P-TEFb could explain our observations. In order to evaluate this activity, an in vitro kinase assay was performed with purified p53 protein and P-TEFb in the presence of different concentrations of ARC. It was found that P-TEFb could phosphorylate p53 (FIG. 3D), indicating that p53 indeed is a substrate for P-TEFb. Also, this phosphorylation decreased in a dose-dependent manner in the presence of ARC (FIG. 3D), demonstrating that ARC inhibits P-TEFb-mediated phosphorylation of p53. In addition, p53 phosphorylated by P-TEFb, but not unphospholylated p53, bound to DNA in a gel shift assay (FIG. 3E), indicating that P-TEFb is both necessary and sufficient to induce DNA binding ability of p53 in vitro. Addition of ARC inhibited this process in a dose-dependent manner (FIG. 3E), implying that this could partly be the mechanism by which the DNA binding ability of p53 is attenuated in vivo.

Example 4

ARC Induces Apoptosis in Transformed and Cancer but not Normal Cells

Flavopiridol and DRB have been shown to cause apoptosis of cancer cells [11, 25]. The ability of ARC to induce apoptosis in wild type and SV40-transformed MRC-5 human fetal lung fibroblasts was evaluated. Twenty-four hours after treatment with ARC, transformed fibroblasts underwent robust apoptosis (around 50% and 70%, respectively, with 5 and 10 μM of ARC) (FIGS. 4A and B). However, the wild type fibroblasts were not susceptible to ARC-mediated cell killing, even at 10 or 20 μM of ARC (FIG. 4A). The appearance of cleaved caspase-3 was observed upon ARC treatment in transformed but not in normal fibroblasts (FIG. 4C), clearly demonstrating that ARC promotes apoptosis specifically in transformed cell types. Interestingly, several-fold higher levels of survivin were observed in transformed fibroblasts when compared to the wild type, and these levels were further reduced after ARC treatment in both cell types (FIG. 4C). The transformed cell types may be more dependent on the survivin levels for their survival than their wild type counterparts and thus the reduction in these levels could be lethal to these cells.

Moreover, the effect of 20 μM ARC treatment on wild type fibroblasts was analyzed and little change was found in the cell cycle profile after 24 hours (data not shown) and the cells undergo G2-arrest after 48 hours (FIG. 4D). These results indicate that while ARC induces efficient apoptosis in transformed cells, it causes a cell cycle block in the normal cells, making it an ideal candidate for anti-cancer drug development.

In order to further characterize ARC with respect to its apoptotic potential, cell lines derived from cancers of different origin were utilized. MCF-7 breast cancer cells underwent apoptosis (around 45% and 55%, respectively, with 10 and 20 μM of ARC) after 24 hours of treatment (FIGS. 5A and 5B). Moreover, cleavage of caspase-9 upon ARC treatment was observed in these cells (FIG. 5C) suggesting that these cells undergo caspase-mediated apoptosis. To evaluate the extent to which ARC-mediated apoptosis is p53-dependent, an MCF-7 cell line that stably expresses a short hairpin RNA (shRNA) targeting p53 (MCF-7-p53si) was used [26]. Cleavage of caspase-9 was detected, even in the absence of p53 in MCF-7-p53si cells (FIG. 5D) indicating that cell death mediated by ARC is p53-independent.

To determine the extent to which ARC induces apoptosis of other cancer cells, different cell lines (LIM1215 colon cancer, AGS gastric cancer and HepG2 liver cancer cells) were treated with ARC for 48 hours and apoptosis (data not shown) and cleavage of caspase-3 were detected (FIG. 5E). Also HepG2 cell line with stable knock-down of p53 (HepG2-p53si) [26] showed cleavage of caspase-3 confirming that ARC-mediated apoptosis is p53-independent (FIG. 5E).

In order to evaluate the extent to which ARC induces apoptosis relative to that of the other known nucleoside analog DRB, LIM1215 colon cancer cells were treated with either ARC or DRB for 48 hours. Using PI staining followed by Flow Cytometry, it was found that 5 μM of ARC treatment resulted in 37.8% apoptosis, while a 50 μM of DRB treatment only showed 23.4% apoptosis (FIG. 5F) suggesting that ARC is more efficient in eliciting apoptosis than DRB at least in these LIM1215 cells.

Example 5

ARC is a Potent Anti-Angiogenic Agent In Vitro

Next, the ability of ARC to inhibit angiogenesis (a process of blood vessel formation that is necessary for tumors in vivo) was evaluated. For this purpose, the compound ARC was sent to NCI/DTP where three types of angiogenesis assays (cord formation assay, motility assay and proliferation inhibition assay) were performed. Human umbilical vein endothelial cells (HUVECs) which are similar to the endothelial cells that line the blood vessels are used for these assays. Normal endothelial cells in vivo divide very rarely (once about every three years on the average), except during tumor development when they divide actively contributing to the growth of new network of blood vessels. Therefore, any inhibition of their growth and motility by ARC in vitro indicates that ARC is an anti-angiogenic agent.

For cord formation assay, HUVECs were plated on a three dimensional layer of Matrigel, where the cells formed cord-like structures. Later, the cells were treated with vehicle (DMSO) or different concentrations of ARC for 24 hours, after which cord formation was quantitated as a function of cord junctions and cord length. A dose dependent decrease was seen in response to ARC treatment in both junction and length (FIG. 6A) with respective $IC_{50}$ values of about 345 and about 382 nM (averages from three trials). These values are about half of what was observed for TNP-470, an exclusive anti-angiogenic agent in clinical trials [27], for which the $IC_{50}$ is about 700 nM [28], suggesting that ARC is a more potent angiogenesis inhibitor in this assay.

For motility assay, HUVECs were pretreated for 24 hours with different concentrations ARC and used in the assay with vascular endothelial growth factor (VEGF) as a chemoattractant. ARC induced a dose dependent reduction in cell motility (FIG. 6B) with an $IC_{50}$ value of about 830 nM (average from two trials). This value is comparable to that of TNP-470, which has an $IC_{50}$ of about 600 nM [28].

For proliferation inhibition assay, HUVECs were grown in the absence of growth factors for 24 hours and then stimulated with 10 ng/ml VEGF and were treated with either DMSO or different concentrations of ARC for 24 hours, 48 hours or 72 hours. ARC inhibited HUVEC growth in a time and concentration dependent manner (FIG. 6C) with an $IC_{50}$ of about 47 nM (average from two trials).

Taken together, these data indicate that ARC is a potent anti-angiogenic agent.

Example 6

ARC May Cause Mitochondrial Injury and Eventual Apoptosis

Figure 7:
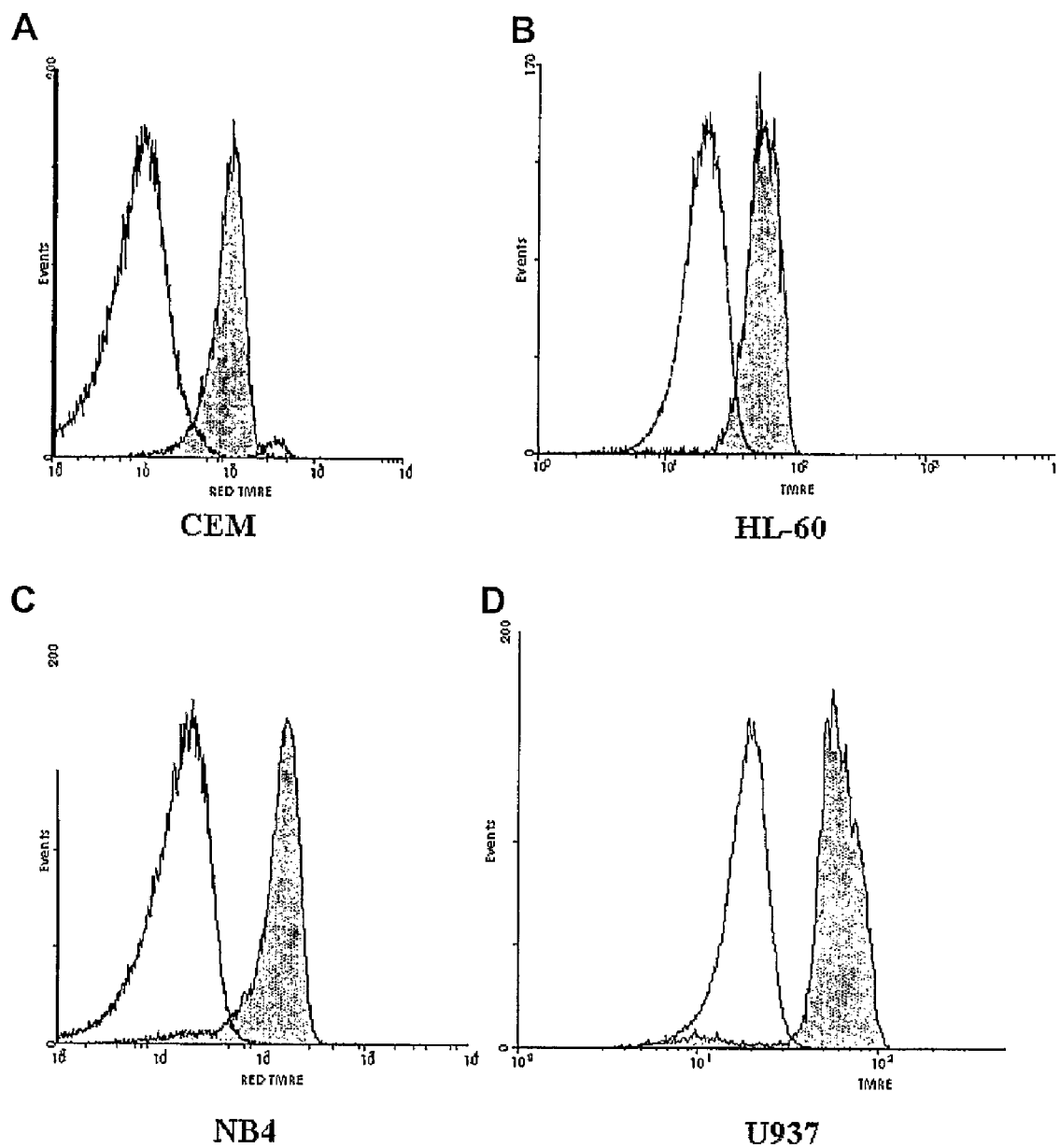
FIG. 7. ARC induces mitochondrial injury in leukemia cells. Different leukemia cells were either treated with DMSO (gray) or 5 μM ARC (white) for 24 hours, stained with TMRE (tetramethyl rhodamine ethyl ester) and subjected to flow cytometry. CEM cells are shown in panel (A), HL-60 in panel (B), NB4 in panel (C) and U937 in panel (D). The shift in the peak from right (DMSO; gray) to left (ARC-treated; white) is due to the lower intake of the dye caused by the loss in mitochondrial potential.
Figure 8:
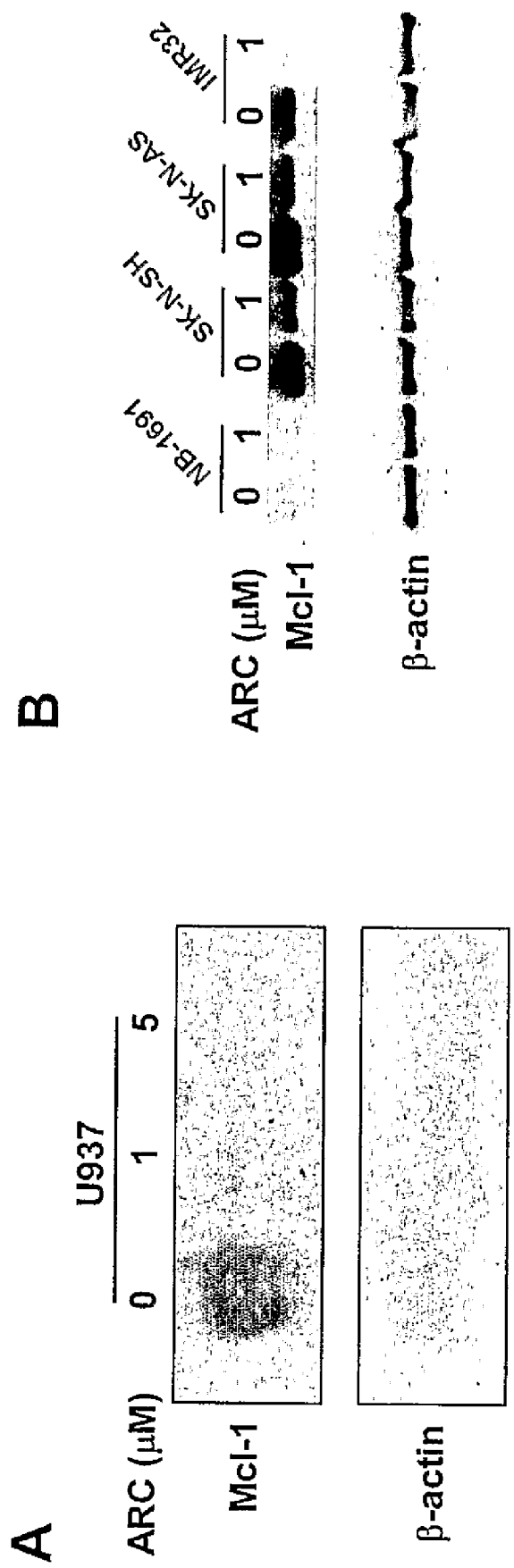
FIG. 8. ARC downregulates Mcl-1 levels in different cancer cells. (A) U937 leukemia cells were treated with different concentrations of ARC as indicated for 24 hours and the cell lysates were probed for Mcl-1 levels. (B) Neuroblastoma cell lines were treated either with DMSO or 1 μM ARC for 24 hours and levels of Mcl-1 were assessed by immunoblotting.

In order to further probe the mechanism of ARC-induced apoptosis, whether or not ARC causes mitochondrial injury was investigated. Permeabilization of mitochondria, followed by cytochrome c release has previously been observed for transcriptional inhibitor flavopiridol [54]. For this analysis, leukemia cell lines CEM, HL-60, NB4 and U937 were treated with either DMSO or ARC. Staining of the mitochondria in these cells by tetramethyl rhodamine ethyl ester (TMRE) followed by flow cytometry revealed that ARC is able to cause mitochondrial depolarization (FIG. 7). These data suggest that ARC targets a step that is upstream of mitochondria to induce apoptosis. It is well known that the Bcl2 family members (eg., Bcl-2, Bcl-XL, Mcl-1) protect the mitochondrial integrity, thereby acting in an anti-apoptotic manner [55]. It is possible that ARC modulates the expression of one or more of these proteins to cause mitochondrial injury. While no changes in the levels of Bcl-2 were detected after ARC treatment (data not shown), Mcl-1 levels were drastically reduced in several different cell lines in response to ARC (FIG. 8).

Figure 9:
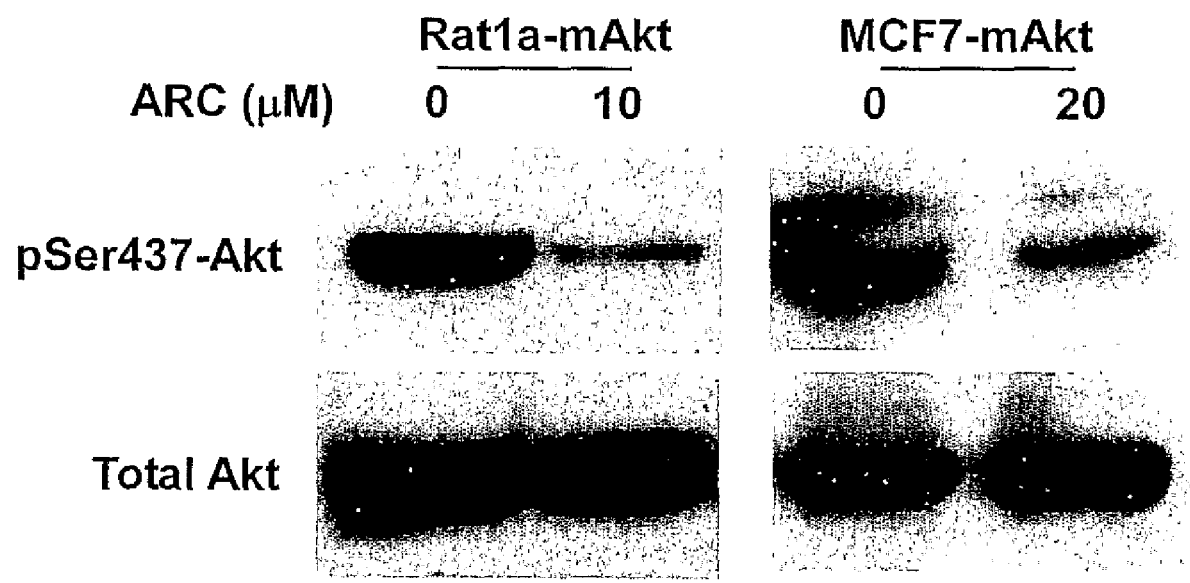
FIG. 9. ARC interferes with the Akt pathway by inhibiting phosphorylation of Akt. Rat1a and MCF-7 cells overexpressing myristoylated-Akt (mAkt) were treated with the indicated concentration of ARC for 24 hours, after which the cell lysates were used for immunoblotting with total and phospho-Ser473 specific Akt antibodies.

Another survival pathway that protects mitochondrial integrity is the Akt (AKT8 virus oncogene cellular homolog) pathway [56]. In order to see if this pathway is affected, two different cell lines that overexpress myrisotylated-Akt (Rat1a-mAkt, and MCF7-mAkt) were used. Myristolated-Akt is a membrane-targeted Akt, a kinase involved in anti-apoptotic signaling. Treatment of ARC led to decrease in Ser473 phosphorylation on Akt in both of these cell lines (FIG. 9), indicating that ARC may also target the Akt signaling pathway to inflict mitochondrial injury and eventual apoptosis.

Example 7

ARC Exhibits Anti-Viral Activity Against HIV In Vitro

Tat, a trans-activator protein produced by human immunodeficiency virus (HIV) plays an important role in HIV life cycle by positively regulating transcription from viral LTR (HIV-1 long-terminal repeat) [51]. It has been shown that Tat specifically mediates transcriptional elongation by recruiting P-TEFb [52, 53]. Therefore blocking P-TEFb is an attractive strategy for inhibiting Tat-mediated transcription that could result in decreased HIV replication. In fact, it was shown that flavopiridol, a P-TEFb inhibitor can efficiently inhibit HIV replication in cell culture [4, 57]. Since ARC is a potent P-TEFb inhibitor, whether or not ARC could antagonize HIV replication was evaluated.

Figure 10:
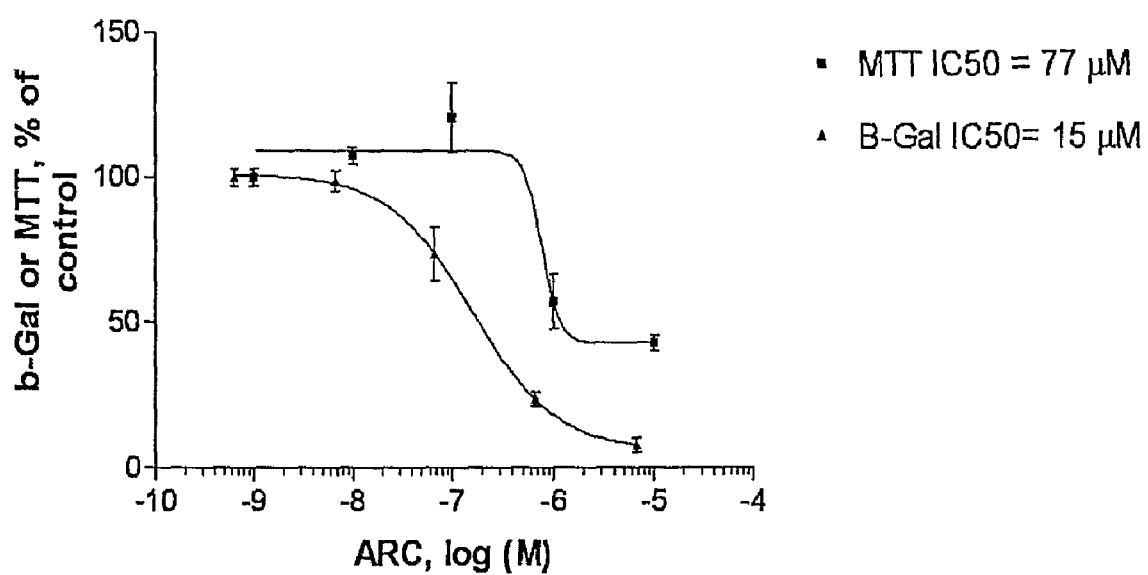
FIG. 10. ARC has antiviral activity against HIV (human immunodeficiency virus) in a cell culture model. HeLa MAGI cells were infected with Adeno-Tat and treated with different amounts of ARC for 18 hours after which, MTT was added to measure cell viability and B-Gal expression was measured by ONPG assay. B-Gal expression is indicative of HIV Tat transactivation ability. Assays were done in quadruplicates.

It was found that ARC efficiently inhibited HIV Tat-mediated transcription in a dose-dependent manner in HeLa MAGI cells (FIG. 10). The rate of transcription was affected more than the viability of cells, demonstrating that ARC specifically inhibits Tat-mediated transcription (FIG. 10). These results suggest that ARC could be useful as an anti-viral agent against HIV and other related viruses.

Discussion and Results

According to the present invention, a novel nucleoside analog ARC was isolated in a screen for inhibitors of p21 transcription. Although ARC reproducibly repressed p21 in several cell lines indicating that the screen was successful, it also suppressed other genes such as hdm2 and survivin (FIGS. 1C-E). Further investigation revealed that ARC is a global transcriptional inhibitor (FIG. 2A). One common feature of the genes repressed by ARC is their short half-life at both the mRNA and protein levels [5]. It has been suggested that induction of p53, accompanied by downregulation of p21 and hdm2, is a hallmark of repression of transcription [16, 25, 29]. This increase in p53 could be due to the downregulation of short-lived protein hdm2, which is a well-established negative regulator of p53 [16, 30]. In agreement with this notion, a similar effect was observed in several cancer cell lines upon treatment with ARC (FIG. 1C).

According to the present invention, ARC and another nucleoside analog DRB, repressed RNA polymerase II transcription to similar levels as measured by nuclear run-on assays (FIG. 2A). One way to repress RNA polymerase II is by direct interaction as seen in the case of α-amanitin [10]. However, treatment of nuclei with ARC in vitro failed to inhibit transcription (FIG. 2B), ruling out its direct interaction with RNA polymerase II. As described herein, ARC employs an indirect mechanism to inhibit transcription, similar to DRB and flavopiridol [4, 31]. Phosphorylation of the CTD of RNA polymerase II by P-TEFb kinase is a requisite step for transcriptional elongation [32, 33] and ARC blocks this process as seen by its inhibition of P-TEFb leading to decreased phosphorylation on RNA polymerase II (FIGS. 2C and 2D). Being an adenosine analog, it seems conceivable that ARC might compete for the ATP-binding site of the P-TEFb kinase leading to its reduced kinase activity (FIG. 2C).

An important aspect of the present invention is that p53 can act as a substrate of phosphorylation by P-TEFb kinase (FIG. 3D). Being a potent P-TEFb inhibitor, ARC was able to block this phosphorylation (FIG. 3D) and subsequent binding of p53 to DNA in vitro (FIG. 3E) and in vivo (FIGS. 3A and 3B). It has been controversial as to the exact requirement of p53 phosphorylation for its DNA binding and transactivation function. Using nutlin-3, a small molecule MDM2 antagonist (which induces p53 without phosphorylation on key serine residues), it was demonstrated that unphosphorylated p53 was equally competent in DNA binding when compared with phosphorylated p53 induced by doxorubicin or etoposide [34]. However, it has also been suggested that phosphorylation of p53 by DNA-PK (DNA-dependent protein kinase) and Chk2 (checkpoint kinase 2) kinases are required for its DNA binding ability after DNA damage induced by ionizing radiation [23, 24]. While Ser-15 on p53 was the target of phosphorylation by DNA-PK, it was not clear which residues are targeted by Chk2 to induce its DNA binding ability [24]. The present description clearly supports the requirement for phosphorylation of p53 for DNA binding. Furthermore, as described herein, it is clear that the phosphorylation of p53 by P-TEFb is necessary and sufficient for this purpose, at least in vitro (FIG. 3E).

Figure 5:
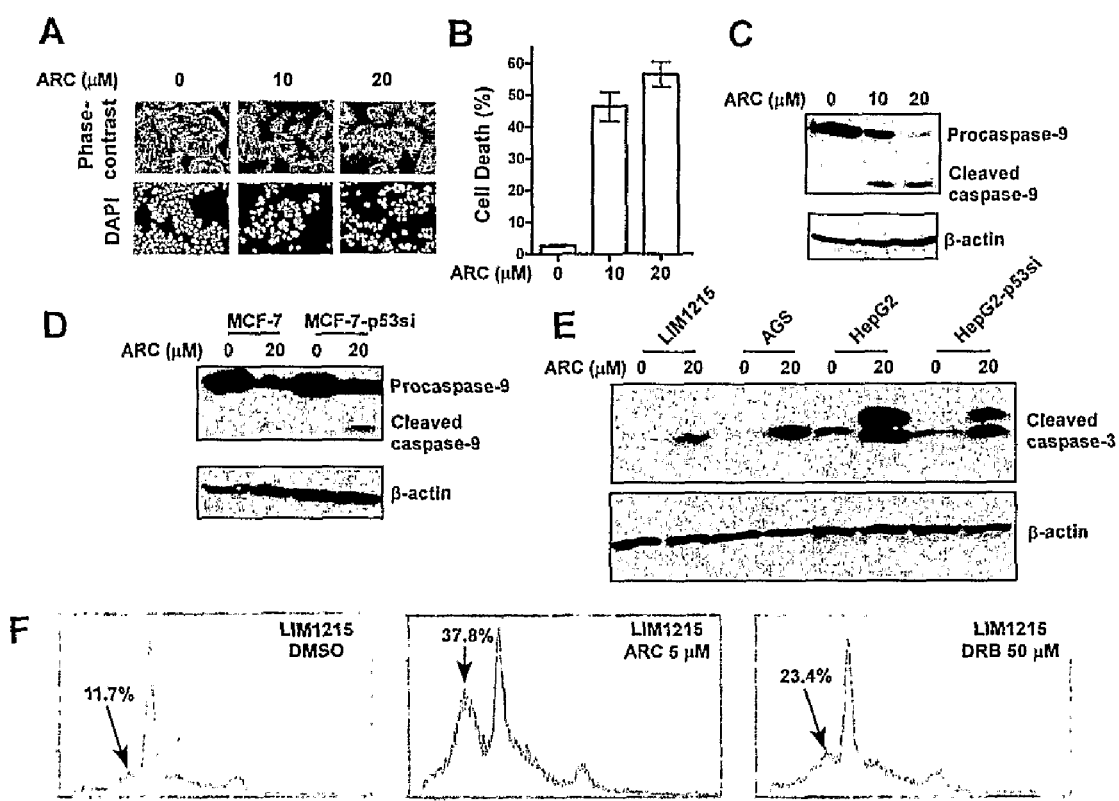
FIG. 5. ARC causes p53-independent apoptosis in various cancer cell lines. (A) Breast cancer cell line MCF-7 was treated with indicated concentrations of ARC for 24 hours. Photographs from phase contrast microscopy (top panel) and fluorescent microscopy after DAPI staining (bottom panel) are shown. (B) Apoptotic nuclei from MCF-7 cells treated with indicated concentrations of ARC for 24 hours were scored after DAPI staining and percentage cell death (Mean±SD; n=3) is shown. (C) Cell lysates were prepared from MCF-7 cells treated with ARC for 24 hours and analyzed for caspase-9 levels by immunoblotting. (D) MCF-7 cells expressing short hairpin RNA targeting p53 (MCF-7-p53si) were compared with wild-type MCF-7 after ARC treatment for 24 hours for the levels of cleaved caspase-9. (E) Cancer cell lines of different origin were treated with 20 μM of ARC for 48 hours and cell lysates were analyzed for the levels of cleaved caspase-3. (F) LIM1215 cells were treated with DMSO, 5 μM ARC and 50 μM DRB as indicated for 48 hours and subjected to flow cytometric analysis after PI staining.

Another noteworthy property of ARC is its ability to induce apoptosis in transformed and various cancer cells (FIGS. 4 and 5). Apoptosis in mammalian cells is a multi-step process that results in the activation of caspases, a subfamily of cysteine proteases, followed by execution of cell death. Due to the lack of functional caspase-3 expression, MCF-7 breast cancer cells do not undergo apoptosis easily [35]. However, the present data indicates that ARC is able to induce efficient apoptosis in MCF-7 cells (FIGS. 5A and 5B), suggesting that ARC invokes a caspase-3-independent cell death pathway in these cells. The other cell lines that were evaluated (SV40-transformed fibroblasts, LIM1215, AGS and HepG2) have caspase-3 expression and thus showed caspase-3 cleavage as a result of ARC treatment (FIGS. 4C and 5E).

A striking feature of ARC-mediated apoptosis is that it is p53-independent. As described herein, MCF-7 and HepG2 cells along with their p53-knocked-down counterparts undergo apoptosis to the same extent (FIGS. 5D, 5E, and data not shown). This is in agreement with the observation that p53 is a marker but not a mediator of flavopiridol-induced cytotoxicity [16]. However, other transcriptional inhibitors DRB and α-amanitin, were suggested to induce p53-dependent apoptosis [25, 29]. It was shown recently that α-amanitin induced apoptosis in the absence of p53-dependent transcription by direct translocation of p53 to mitochondria, a phenomenon which has also been observed by other investigators in different situations [36-38]. As shown herein, however, despite the accumulation of transcriptionally incompetent p53 as seen by its inability to induce its target genes (FIGS. 1A and 1B) and to bind DNA (FIGS. 2A and 2B) in response to ARC treatment, it did not lead to enhanced apoptosis. The reason for this discrepancy is unclear. The differences in the cell lines or approaches used herein could be the reason behind the difference in outcome. Also, since α-amanitin represses transcription by a different mechanism than ARC, its mode of inducing apoptosis could be different.

Although, as described herein, ARC causes p53-independent, caspase-mediated, apoptosis, the precise step that is targeted by ARC to elicit this response is presently unknown. The downregulation of Mcl-1 (myeloid cell leukemia 1), a short-lived anti-apoptotic protein, was suggested as a possible mechanism of flavopiridol-induced apoptosis in leukemia cells [39]. It is reasonable to conclude that the ability of ARC to downregulate anti-apoptotic proteins including, but not limited to survivin and p21 (FIGS. 1C and 4C), plays an important role mechanistically. Survivin, a member of the mammalian IAP (Inhibitor of Apoptosis Proteins) family is overexpressed in a variety of tumors and has been proposed as an attractive target for cancer therapy [40, 41]. It was found that survivin expression increased gradually in the transition from normal colorectal mucosas to adenomas with low grade dysplasia to high grade dysplasia/carcinomas [42]. In agreement with this fact, higher levels of survivin expression were observed in the SV40-transformed fibroblasts when compared to the wild type fibroblasts (FIG. 4C). Apart from apoptosis inhibition, survivin also plays an important role in mitosis [41]. Accordingly, it is possible that the low levels of ARC in wild type fibroblasts, when further downregulated by ARC, resulted in G2 block (FIG. 4D), due to the inability of the cells to proceed to mitosis. However, in the SV40-transformed fibroblasts, survivin may primarily be anti-apoptotic, thus leading to cell death when these levels are downregulated by ARC (FIGS. 4A-C).

Similarly, p21 may also act in an anti-apoptotic fashion by inducing cell-cycle arrest or by inhibiting pro-apoptotic molecules such as procaspase-3 and apoptosis signal-regulating kinase1 (ASK1) [43, 44]. It has been suggested that inhibition of p21 may be an effective strategy for enhancing apoptosis in cancer cells mediated by anti-cancer agents [17-19, 45, 46]. The fact that ARC represses both survivin and p21 makes a strong case for consideration of ARC as a potential anti-tumor agent. This is further supported by the observation that ARC was >10-fold more efficient in inducing apoptosis than the other nucleoside analog DRB (FIG. 5F). This is especially intriguing because, as shown herein, ARC and DRB repress global transcription to similar extent (FIG. 2A). The difference in apoptosis suggests that ARC, apart from transcriptional repression, might employ additional means of inducing cell death. The present results also suggest that ARC is anti-angiogenic in nanomolar concentrations in vitro, and its activity is comparable to TNP-470 [28]. Preliminary toxicity studies from NCI/DTP indicate that concentrations as high as 200 mg/Kg were non-toxic to B6D2FI mice during a 5-day period.

In summary, the ability of the nucleoside compounds of the present invention to induce apoptosis in transformed cells and cancer cells, but not normal cells, along with their potent anti-angiogenic activity, make these nucleoside compounds ideally suited for anti-cancer and/or anti-angiogenic treatment and drug development.

In addition, nucleoside compounds according to the present invention can be used as antiviral agents, as reagents for inhibiting cyclin-dependent kinase (CDK) activity, as inhibitors of general transcription, and as inhibitors of phosphorylation and DNA-binding activity of p53.

Numerous variations and modifications of the embodiments described above may be effected without departing from the spirit and scope of the novel features of the invention. No limitations with respect to the specific embodiments illustrated herein are intended or should be inferred.

PUBLICATIONS

1. Boeger, H., Bushnell, D. A., Davis, R., Griesenbeck, J., Lorch, Y., Strattan, J. S., Westover, K. D., and Kornberg, R. D. (2005). Structural basis of eukaryotic gene transcription. *FEBS Letters* 579, 899-903.
2. Shilatifard, A., Conaway, R. C., and Conaway, J. W. (2003). The RNA polymerase II elongation complex. *Annu. Rev. Biochem.* 72, 693-715.
3. Sobell, H. M. (1985). Actinomycin and DNA transcription. *Proc. Natl. Acad. Sci. U.S.A.* 82, 5328-5331.
4. Chao, S. H., and Price, D. H. (2001). Flavopiridol inactivates P-T1Fb and blocks most RNA polymerase II transcription in vivo. *J. Biol. Chem.* 276, 31793-31799.
5. Lam, L. T., Pickeral, O. K., Peng, A. C., Rosenwald, A., Hurt, E. M., Giltnane, J. M., Averett, L. M., Zhao, H., Davis, R. E., Sathyamoorthy, M., Wahl, L. M., Harris, E. D., Mikovits, J. A., Monks, A. P., Hollingshead, M. G., Sausville, E. A., and Staudt, L. M. (2001). Genomic-scale measurement of mRNA turnover and the mechanisms of action of the anti-cancer drug flavopiridol. *Genzonle Biol.* 2, RESEARCH0041.
6. de Azevedo, W. F., Jr., Canduri, F., and da Silveira, N. J. (2002). Structural basis for inhibition of cyclin-dependent kinase 9 by flavopiridol. *Biochem. Biophys. Res. Commun.* 293, 566-571.
7. Rudd, M. D., and Luse, D. S. (1996). Amanitin greatly reduces the rate of transcription by RNA polymerase II ternary complexes but fails to inhibit some transcript cleavage modes. *J. Biol. Chem.* 271, 21549-21558.
8. Chafin, D. R., Guo, H., and Price, D. H. (1995). Action of alpha-amanitin during pyrophosphorolysis and elongation by RNA polymerase II. *J. Biol. Chem.* 270, 19114-19119.
9. Wieland, T., and Faulstich, H. (1991). Fifty years of amanitin. *Experientia* 47, 1186-1193.
10. Bushnell, D. A., Cramer, P., and Kornberg, R. D. (2002). Structural basis of transcription: alpha-amanitin-PNA polymerase II cocrystal at 2.8 A resolution. *Proc. Natl. Acad. Sci. U.S.A.* 99, 1218-1222.
11. Blagosklonny, M. V. (2004). Flavopiridol, an inhibitor of transcription: implications, problems and solutions. *Cell Cycle* 3, 1537-1542.
12. Chao, S. H., Fujinaga, K., Marion, J. E., Taube, R., Sausville, E. A., Senderowicz, A. M., Peterlin, B. M., and Price, D. H. (2000). Flavopiridol inhibits P-TEFb and blocks HIV-1 replication. *J. Biol. Chem.* 275, 28345-28348.
13. Grant, S., and Dent, P. (2004). Gene profiling and the cyclin-dependent kinase inhibitor flavopiridol: what's in a name? *Mol. Cancer Ther.* 3, 873-875.
14. Newcomb, E. W. (2004). Flavopiridol: pleiotropic biological effects enhance its anti-cancer activity. Anticancer Drugs 15, 411-419.
15. Senderowicz, A. M. (1999). Flavopiridol: the first cyclin-dependent kinase inhibitor in human clinical trials. Invest. New Drugs 17, 313-320.
16. Demidenko, Z. N., and Blagosklonny, M. V. (2004). Flavopiridol induces p53 via initial inhibition of Mdm2 and p21 and, independently of p53, sensitizes apoptosis-reluctant cells to tumor necrosis factor. *Cancer Res.* 64, 3653-3660.
17. Tian, H., Wittmack, E. K., and Jorgensen, T. J. (2000). p21WAF1/CIP1 antisense therapy radiosensitizes human colon cancer by converting growth arrest to apoptosis. *Cancer Res.* 60, 679-684.
18. Chattopadhyay, D., Ghosh, M. K., Mal, A., and Harter, M. L. (2001). Inactivation of p21 by E IA leads to the induction of apoptosis in DNA-damaged cells. *J. Virol.* 75, 9844-9856.
19. Javelaud, D., and Besancon, F. (2002). Inactivation of p21WAF1 sensitizes cells to apoptosis via an increase of both p14ARF and p53 levels and an alteration of the Bax/Bcl-2 ratio. *J. Biol. Chem.* 277, 37949-37954.
20. Arango, D., Mariadason, J. M., Wilson, A. J., Yang, W., Corner, G. A., Nicholas, C., Aranes, M. J., and Augenlicht, L. H. (2003). c-Myc overexpression sensitises colon cancer cells to camptothecin-induced apoptosis. *Br. J. Cancer* 89, 1757-1765.
21. Seoane, J., Le, H. V., and Massague, J. (2002). Myc suppression of the p21(Cip1) Cdk inhibitor influences the outcome of the p53 response to DNA damage. *Nature* 419, 729-734.
22. Tishler, R. B., Calderwood, S. K., Coleman, C. N., and Price, B. D. (1993). Increases in sequence specific DNA binding by p53 following treatment with chemotherapeutic and DNA damaging agents. *Cancer Res.* 53, 2212-2216.
23. Woo, R. A., McLure, K. G., Lees-Miller, S. P., Rancourt, D. E., and Lee, P. W. (1998). DNA-dependent protein kinase acts upstream of p53 in response to DNA damage. *Nature* 394, 700-704.
24. Jack, M. T., Woo, R. A., Motoyama, N., Takai, H., and Lee, P. W. (2004). DNA-dependent protein kinase and checkpoint kinase 2 synergistically activate a latent population of p53 upon DNA damage. *J. Biol. Chem.* 279, 15269-15273.
25. te Poele, R. H., Okorokov, A. L., and Joel, S. P. (1999). RNA synthesis block by 5, 6-dichloro-1-beta-D-ribofuranosylbenzimidazole (DRB) triggers p53-dependent apoptosis in human colon carcinoma cells. *Oncogene* 18, 5765-5772.
26. Radhakrishnan, S. K., Gierut, J., and Gartel, A. L. Multiple alternate p21 transcripts are regulated by p53 in human cells. *Oncogene*, In Press.
27. Folkman, J. (2004). Endogenous angiogenesis inhibitors. *Apmis* 112, 496-507.
28. Adams, B. K., Ferstl, E. M., Davis, M. C., Herold, M., Kurtkaya, S., Camalier, R. F., Hollingshead, M. G., Kaur, G., Sausville, E. A., Rickles, F. R., Snyder, J. P., Liotta, D. C., and Shoji, M. (2004). Synthesis and biological evaluation of novel curcumin analogs as anti-cancer and anti-angiogenesis agents. *Bioorg. Med. Chem.* 12, 3871-3883.
29. Arima, Y., Nitta, M., Kuninaka, S., Zhang, D., Fujiwara, T., Taya, Y., Nakao, M., and Saya, H. (2005). Transcriptional blockade induces p53-dependent apoptosis associated with translocation of p53 to mitochondria. *J. Biol. Chem.* 280, 19166-19176.
30. Kubbutat, M. H., Jones, S. N., and Vousden, K. H. (1997). Regulation of p53 stability by Mdn2. *Nature* 387, 299-303.
31. Marshall, N. F., and Price, D. H. (1995). Purification of P-TEFb, a transcription factor required for the transition into productive elongation. *J. Biol. Chem.* 270, 12335-12338.
32. Price, D. H. (2000). P-TEFb, a cyclin-dependent kinase controlling elongation by RNA polymerase II. *Mol. Cell. Biol.* 20, 2629-2634.
33. Peng, J., Liu, M., Marion, J., Zhu, Y., and Price, D. H. (1998). RNA polymerase II elongation control. *Cold Spring Harb. Symp. Quant. Biol.* 63, 365-370.
34. Thompson, T., Tovar, C., Yang, H., Carvajal, D., Vu, B. T., Xu, Q., Wahl, G. M., Heimbrook, D. C., and Vassilev, L. T. (2004). Phosphorylation of p53 on key serines is dispensable for transcriptional activation and apoptosis. *J. Biol. Chem.* 279, 53015-53022.
35. Janicke, R. U., Sprengart, M. L., Wati, M. R., and Porter, A. G. (1998). Caspase-3 is required for DNA fragmentation and morphological changes associated with apoptosis. *J. Biol. Chem.* 273, 9357-9360.
36. Chipuk, J. E., Kuwana, T., Bouchier-Hayes, L., Droin, N. M., Newmeyer, D. D., Schuler, M., and Green, D. R. (2004). Direct activation of Bax by p53 mediates mitochondrial membrane permeabilization and apoptosis. *Science* 303, 1010-1014.
37. Erster, S., Mihara, M., Kim, R. H., Petrenko, O., and Moll, U. M. (2004). In vivo mitochondrial p53 translocation triggers a rapid first wave of cell death in response to DNA damage that can precede p53 target gene activation. *Mol. Cell. Biol.* 24, 6728-6741.
38. Chipuk, J. E., Maurer, U., Green, D. R., and Schuler, M. (2003). Pharmacologic activation of p53 elicits Bax-dependent apoptosis in the absence of transcription. *Cancer Cell* 4, 371-381.
39. Chen, R., Keating, M. J., Gandhi, V., and Plunkett, W. (2005). Transcription inhibition by flavopiridol: mechanism of chronic lymphocytic leulkemia cell death. *Blood* 106, 2513-2519.
40. Altieri, D. C. (2003). Validating survivin as a cancer therapeutic target. Nat Rev *Cancer* 3, 46-54.
41. Altieri, D. C. (2003). Survivin, versatile modulation of cell division and apoptosis in cancer. *Oncogene* 22, 8581-8589.
42. Lin, L. J., Zheng, C. Q., Jin, Y., Ma, Y., Jiang, W. G., and Ma, T. (2003). Expression of survivin protein in human colorectal carcinogenesis. *World J. Gastroenterol.* 9, 974-977.
43. Suzuki, A., Tsutomi, Y., Akahane, K., Araki, T., and Miura, M. (1998). Resistance to Fas-mediated apoptosis: activation of caspase 3 is regulated by cell cycle regulator p21 WAF 1 and IAP gene family ILP. *Oncogene* 17, 931-939.
44. Asada, M., Yamada, T., Ichijo, H., Delia, D., Miyazono, K., Fukumuro, K., and Mizutani, S. (1999). Apoptosis inhibitory activity of cytoplasmic p21(Cip1/WAF1) in monocytic differentiation. *Embo. J.* 18, 1223-1234.
45. Gartel, A. L., and Radhakrishnan, S. K. (2005). Lost in transcription: p21 repression, mechanisms, and consequences. *Cancer Res.* 65, 3980-3985.
46. Gartel, A. L., and Tyner, A. L. (2002). The role of the cyclin-dependent kinase inhibitor p21 in apoptosis. *Mol. Cancer. Ther.* 1, 639-649.
47. Radhakrishnan, S. K., and Gartel, A. L. (2005). The PPAR-gamma agonist pioglitazone post-transcriptionally induces p21 in PC3 prostate cancer but not in other cell lines. *Cell Cycle* 4, 582-584.
48. Gartel, A. L., Feliciano, C., and Tyner, A. L. (2003). A new method for determining the status of p53 in tumor cell lines of different origin. *Oncol. Res.* 13, 405-408.
49. Radhakrishnan, S. K., Feliciano, C. S., Najmabadi, F., Haegebarth, A., Kandel, E. S., Tyner, A. L., and Gartel, A. L. (2004). Constitutive expression of E2F-1 leads to p21-dependent cell cycle arrest in S phase of the cell cycle. *Oncogene* 23, 4173-4176.

50. Kaur, G., Belotti, D., Burger, A. M., Fisher-Nielson, K., Borsotti, P., Riccardi, E., Thillainathan, J., Hollingshead, M., Sausville, E. A., and Giavazzi, R. (2004). Antiangiogenic properties of 17-(dimethylaminoethylamino)-17-demethoxygeldanamycin: an orally bioavailable heat shock protein 90 modulator. *Clin. Cancer Res.* 10, 4813-4821.

51. Strebel, K. (2003). Virus-host interactions: role of HIV proteins Vif, Tat, and Rev. *Aids* 17 Suppl 4, S25-34.

52. Deng, L., Ammosova, T., Pumfery, A., Kashanchi, F., and Nekhai, S. (2002). HIV-1 Tat interaction with RNA polymerase II C-terminal domain (CTD) and a dynamic association with CDK2 induce CTD phosphorylation and transcription from HIV-1 promoter. *J. Biol. Chem.* 277, 33922-33929.

53. Mancebo, H. S., Lee, G., Flygare, J., Tomassini, J., Luu, P., Zhu, Y., Peng, J., Blau, C., Hazuda, D., Price, D., and Flores, O. (1997). P-TEFb kinase is required for HIV Tat transcriptional activation in vivo and in vitro. *Genes Dev.* 11, 2633-2644.

54. Newcomb, E. W., Tamasdan, C., Entzminger, Y., Alonso, J., Friedlander, D., Crisan, D., Miller, D. C., and Zagzag, D. (2003). Flavopiridol induces mitochondrial-mediated apoptosis in murine glioma GL261 cells via release of cytochrome c and apoptosis inducing factor. *Cell Cycle* 2, 243-250.

55. Martinou, J. C., and Green, D. R. (2001). Breaking the mitochondrial barrier. *Nat. Rev. Mol Cell Biol.* 2, 63-67.

56. Kennedy, S. G., Kandel, E. S., Cross, T. K., and Hay, N. (1999). Akt/Protein kinase B inhibits cell death by preventing the release of cytochrome c from mitochondria. *Mol. Cell. Biol.* 19, 5800-5810.

57. Chao, S. H., Fujinaga, K., Marion, J. E., Taube, R., Sausville, E. A., Senderowicz, A. M., Peterlin, B. M., and Price, D. H. (2000). Flavopiridol inhibits P-TEFb and blocks HIV-1 replication. *J. Biol. Chem.* 275, 28345-28348.

58. Blight, K. J., Kolykhalov, A. A., and Rice, C. M. (2000). Efficient initiation of HCV RNA replication in cell culture. *Science* 290, 1972-1974.

What is claimed is:

1. A method for inhibiting tumor cell growth comprising the step of contacting a tumor cell with a nucleoside derivative in an amount sufficient to inhibit growth of the tumor cell, wherein the nucleoside derivative has the formula:

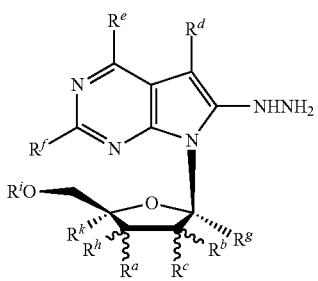

or a pharmaceutically acceptable salt thereof;
wherein $R^a$, $R^b$, $R^c$ and $R^h$ are each independently hydrogen, cyano, azido, halogen, hydroxy, mercapto, amino, $C_{1-4}$ alkoxy, $C_{2-4}$ alkenyl, $C_{2-4}$ alkynyl, or $C_{1-4}$ alkyl, wherein alkyl is unsubstituted or substituted with hydroxy, amino, $C_{1-4}$ alkoxy, $C_{1-4}$ alkylthio, or one to three fluorine atoms, or $R^b$ and $R^c$ together with the carbon atom to which they are attached form a 3- to 6-membered saturated monocyclic ring system optionally containing a heteroatom that is O, S or $NC_{0-4}$ alkyl;
$R^d$ is nitro, $C_{1-3}$ alkyl, $NHCONH_2$, $CONR^jR^j$, $CSNR^jR^j$, $COOR^j$, $C(=NH)NH_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl) or (imidazol-2-yl), wherein alkyl is unsubstituted or substituted with one to three groups that are independently halogen, amino, hydroxy, carboxy or $C_{1-3}$ alkoxy;
$R^e$ and $R^f$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, or $C_{4-6}$ cycloheteroalkyl, unsubstituted or substituted with one to two groups that are independently halogen, hydroxy, amino, $C_{1-4}$ alkyl or $C_{1-4}$ alkoxy;
$R^i$ is hydrogen, $C_{1-10}$ alkylcarbonyl, $P_3O_9H_4$, $P_2O_6H_3$, or $P(O)R^mR^n$;
each $R^j$ is independently hydrogen or $C_{1-6}$ alkyl;
$R^k$ and $R^g$ are each independently hydrogen, methyl, hydroxymethyl or fluoromethyl; and
$R^m$ and $R^n$ are each independently hydroxy, $OCH_2CH_2SC(=O)C_{1-4}$ alkyl, $OCH_2O(C=O)OC_{1-4}$ alkyl, $NHCHMeCO_2Me$, or $OCH(C_{1-4}$ alkyl)$O(C=P)C_{1-4}$ alkyl, wherein alkyl is unsubstituted or substituted with one to three groups that are independently halogen, amino, hydroxy, carboxy, or $C_{1-3}$ alkoxy.

2. The method of claim 1 wherein transcription is inhibited in the tumor cell.

3. The method of claim 1 wherein $R^d$ is $CONH_2$.

4. The method of claim 1 wherein $R^e$ is $NH_2$ and $R^f$ is H.

5. The method of claim 1 wherein $R^a$ and $R^c$ are each hydroxyl, and $R^b$, $R^g$, $R^h$ and $R^i$ are each H.

6. A method for inhibiting tumor cell growth comprising the step of contacting a tumor cell with a nucleoside derivative in an amount sufficient to inhibit growth of the tumor cell, wherein the nucleoside derivative has the formula:

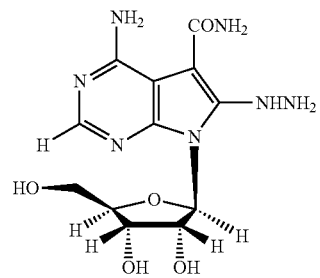

or a pharmaceutically acceptable salt thereof.

7. The method of claim 1, wherein the tumor cell is a colon tumor cell, a breast tumor cell, a liver tumor cell, a lung tumor cell, or a gastric tumor cell.

8. The method of claim 7, wherein the tumor cell is a human tumor cell.

9. The method of claim 2, wherein transcription inhibition in the tumor cell differentially affects one or more short half-life transcripts that are overexpressed in the tumor cell.

10. The method of claim 9, wherein the one or more short half-life transcripts encode Mcl-1.

11. The method of claim 10 wherein the tumor cell is undergoing apoptosis.

12. The method of claim 9, wherein the one or more short half-life transcripts encode survivin.

13. The method of claim 12, wherein the tumor cell is undergoing apoptosis.

14. The method of claim 6, wherein the tumor cell is a colon tumor cell, a breast tumor cell, a liver tumor cell, a lung tumor cell, or a gastric tumor cell.

15. The method of claim 14, wherein the tumor cell is a human tumor cell.

16. The method of claim 6, wherein transcription is inhibited in the tumor cell.

17. The method of claim 16, wherein transcription inhibition in the tumor cell differentially affects one or more short half-life transcripts that are overexpressed in the tumor cell.

18. The method of claim 17, wherein the one or more short half-life transcripts encode Mcl-1.

19. The method of claim 18 wherein the tumor cell is undergoing apoptosis.

20. The method of claim 17, wherein the one or more short half-life transcripts encode survivin.

21. The method of claim 20, wherein the tumor cell is undergoing apoptosis.

* * * * *